(12) United States Patent
Kopelman et al.

(10) Patent No.: US 6,845,175 B2
(45) Date of Patent: Jan. 18, 2005

(54) DENTAL IMAGE PROCESSING METHOD AND SYSTEM

(75) Inventors: Avi Kopelman, Tel Aviv (IL); Eldad Taub, Reut (IL)

(73) Assignee: Cadent Ltd., Or Yehuda (IL)

(*) Notice: Subject to any disclaimer, the term of this patent is extended or adjusted under 35 U.S.C. 154(b) by 479 days.

(21) Appl. No.: 09/830,264

(22) Filed: Apr. 23, 2001

(65) Prior Publication Data

US 2003/0169913 A1 Sep. 11, 2003

Related U.S. Application Data

(63) Continuation of application No. PCT/IL99/00577, filed on Nov. 1, 1999.

(30) Foreign Application Priority Data

Nov. 1, 1998 (IL) ................................. 126838

(51) Int. Cl.[7] .............................................. G06K 9/00
(52) U.S. Cl. ..................... 382/154; 382/294; 128/922
(58) Field of Search ........................ 382/128, 131, 382/154, 285, 294; 600/587, 589, 590; 128/922; 433/24, 29, 68, 69, 215

(56) References Cited

U.S. PATENT DOCUMENTS

| 5,151,856 | A | | 9/1992 | Halmann et al. |
| 5,278,756 | A | | 1/1994 | Lemchen et al. |
| 5,318,441 | A | * | 6/1994 | Keller ......................... 433/68 |
| 6,068,482 | A | * | 5/2000 | Snow .......................... 433/223 |
| 6,081,739 | A | * | 6/2000 | Lemchen ..................... 600/407 |

FOREIGN PATENT DOCUMENTS

| DE | 4141311 | 8/1993 |
| EP | 0488987 | 6/1992 |
| EP | 0741994 | 11/1996 |
| JP | 4-336048 | 11/1992 |
| WO | WO 97/03622 | 2/1997 |
| WO | 01/80761 A2 | 11/2001 |

OTHER PUBLICATIONS

International Search Report for International Application No. PCT/ IL 99/00577, mailed on Feb. 17, 2000.

An English language title and abstract is provided for DE 4141311.

* cited by examiner

Primary Examiner—Todd E. Manahan
(74) Attorney, Agent, or Firm—Nath & Associates PLLC; Gary M. Nath; Lee C. Heiman

(57) ABSTRACT

An image processing method for use in dentistry or orthodontic is provided. Two images of teeth, one being a two-dimensional image and one a three-dimensional image are combined in a manner to allow the use of information obtained from one to the other. In order to combine the two images a set of basic landmarks is defined in one, identified in the other and then the two images are registered.

23 Claims, 11 Drawing Sheets

DENTAL IMAGE PROCESSING METHOD AND SYSTEM

This is a continuation of prior International application number PCT/IL99/00577, filed Nov. 1, 1999 which is hereby incorporated herein by reference in its entirety.

FIELD OF THE INVENTION

The present invention is generally in the field of dentistry and provides an image processing method and system useful as a tool by the dentist or orthodont.

BACKGROUND OF THE INVENTION

There are a wide variety of imaging techniques used routinely in orthrdontics. One important imaging technique is the so-called radiographic cephalometric technique. A radiographic cephalometric image is then used for a cephalometric analysis. Such an analysis is essentially a measurement system designed to describe relationships between the various parts of the skeletal, dental and soft tissue elements of the cranofacial complex. The two cephalometric images typically used are a lateral cephalometric image, which is of prime use in orthodontic and a front cephalometric image which is of somewhat less importance.

Cephalometric methods enable to define certain norms of a skeletal, dental and soft tissue of the cranofacial complex. A cephalometric measurement of individuals can then be compared with norms for age, sex and population group. A cephalogram is in effect a two-dimensional representation of a three-dimensional cranofacial structure. It is thus difficult in an analysis performed on such an image to distinguish between bilateral structures to trace them independently. Additionally, facial aspects are not entirely asymmetrical, this may add a further inaccuracy to an analysis of this kind. Other sources of errors in a cephalometric image include different magnification of different aspects depending on the distance from the film and imperfect positioning of the patient in the cephalostat. These all add up to considerable errors in cephalometry.

An orthodont, prior to beginning the orthodontic treatment typically takes a teeth impression on the basis of which a plaster model may be prepared There are known also a number of imaging techniques which allow to obtain, within a computer environment, a virtual three-dimensional image of the teeth. Such techniques are described for example in WO 97/03622 and DE-C-414311. A three-dimensional teeth image provides a different information than that obtained by a cephalometric analysis. Particularly, a virtual teeth image allows better appreciation of the three-dimensional structure of the teeth and the relative position of different teeth.

For the purpose of proper design of orthodontic treatment it would have been high advantageous to have a method and system whereby information which can be acquired from one type of image can be transferred or superpositioned to information available from another type of image.

GENERAL DESCRIPTION OF THE INVENTION

In accordance with the invention a novel method and system is provided in which information and data available from one type of teeth imaging technique is transferred and used in an image obtained by another kind of teeth imaging technique. This transfer of information provides the dentist or the orthodont with a powerful tool for designing of orthodontic treatment.

In accordance with the invention there is provided an image processing method comprising:

(a) applying at least a first imaging technique and a second imagining technique to acquire a first, two-dimensional image of at least a first portion of teeth and a second, three-dimensional virtual image of at least a second portion of the teeth, respectively, there being at least a partial overlap between said first and second portions; and (b) defining a set of basic landmarks in either one of the two images, locating said set in the other of the two images and registering said set in the two images.

By another of its aspects the present invention provides an image processing system comprising:

(i) a first utility for receipt of first data representative of a first two-dimensional image of at least a first teeth portion;

(ii) a second utility for receipt of second data representative of a second three-dimensional virtual image of teeth of at least a second teeth portion;

(iii) a module for defining basic landmarks in both images and for generating data representative thereof; and (iv) a processor associated with said first and said second utility and with said module, for receiving said first and said second data and for mapping elements in one of the two images to the other of the two images according to the data representative of said basic landmarks.

In accordance with one embodiment of the invention, the imaging method and system is used to obtain orthodontic-relevant information, namely information to be used by an orthodont within the framework of an orthodontic treatment or for the design of such a treatment. This embodiment involves a registration of at least two images, one being a three-dimensional virtual image of a teeth model and the other being a two-dimensional image, e.g. a cephalometric image. Occasionally, other images may also be brought into registration consisting, for example of one or more of a lateral videographic image, a frontal videographic image and a frontal cephalometric image.

In accordance with another embodiment of the invention, the method and system are used for proper design of a dental implant or of a crown. For proper placement of an implant, the bone has to be carefully studied beforehand and examined whether it can receive the dental implant In addition, the exact position and orientation of the dental implant has to be properly pre-designed. Typically, for a proper design of an implant, a three-dimensional virtual image of a teeth model is brought into registration with both a lateral cephalometric image and at times also with a frontal cephalometric image. This will allow to properly predict the manner of receipt of the implant within the bones of the jaw.

In the following, the invention will be described with particular reference to imaging for the purpose of design of the orthodontic treatment. It will however be appreciated, that the invention applies, mutatis mutandis also to its application for he purpose of proper design of tooth implants.

The first image is preferably an x-ray image, typically a cephalometric image obtained by radiographic cephalometric technique. The x-ray image is preferably a lateral image although at times the image may be from another orientation, e.g. a frontal image. In a cephalometric image, some facial profile aspects may at times be seen. However, typically, before an orthodontic treatment also a third, side elevational view of the face is taken from the same direction in which the radiographic cephalometric image was obtained. In accordance with an embodiment of the invention, such a third image, comprising at least a profile of facial aspects, is also obtained and used in the imaging technique of the invention. The side elevational image may be obtained, for example, by video cephalometry.

The term "virtual three-dimensional teeth image" refers to an image, represented within the computer environment which consists primarily of the teeth of one or both jaws. For example, a virtual three-dimensional teeth image may be represented in a manner resembling an image of a plaster model. A virtual three-dimensional image may be obtained by a variety of techniques, e.g. those described in the references mentioned above. Particularly, the three-dimensional virtual image may be obtained by the method described in WO 97/03622, which is incorporated herein by reference as an example of the manner of obtaining a three-dimensional virtual image for use in the method and system of the invention. It should be understood that the invention is not limited to a specific type of image obtained by one imaging technique or another. For example, the two-dimensional image may be obtained by a variety of different imaging techniques including magnetic resonance imaging (MRI), computerized tomography (CT) various radio-imaging techniques, etc. Similarly, the three-dimensional teeth image may be obtained by any one of a number of imaging techniques available including those disclosed in the aforementioned references as well as others such as those making use of a scanning probe, various photographic techniques, techniques in which teeth are scanned by a probing light beam, etc.

The term "image" as used herein should not be understood only as referring to the image as acquired in the imaging technique but rather may be also a result of initial image processing, e.g. an image processing intended to define boundaries of various objects in the image. Thus, the term "image" encompasses also a representation, prepared on the basis of an acquired image, of boundaries of objects, e.g. teeth, bones, a profile of facial aspects, etc.

Often, the imaging technique and analysis in accordance with the invention will make use of a third image, which may be the elevational image mentioned above, or any other image useful in improving the orthodontic analysis. Thus, by way of example, where said first image is a lateral two-dimensional image, said third image may be one or both of the afore-mentioned lateral elevational image or a frontal x-ray or videographic image.

The basic landmarks which are used for registering the two sets of images, are typically defined points at either the base or the apex of certain selected teeth e.g. the incisors and the first molars. Such basic landmarks may be selected by the user or may be automatically selected by the system's processor, e.g. based on established norms. After selecting the basic landmarks and marking them in one of the images, then the landmarks may be marked in the other images to allow to register both images. The term "registering" should not necessarily be understood as meaning a physical registration of the two images but rather as meaning the mapping of each feature in one image to a corresponding feature in another. The outcome of such registration is that any manipulation made on one image will yield a corresponding manipulation in the other image. For example, if one image is manipulated by displacing one tooth, this should result in a corresponding displacement of the same tooth in the other image At times it may be desired to view both images on a screen superimposed one on the other. As two or more images have to be superimposed may be presented initially at a different scale, an initial step which is necessary to be taken by the system is to either enlarge or reduce the scale of one image until there is an essential complete overlap of the basic landmarks in the two images. It should however be noted that registering of different images may not necessarily imply superpositioning, but rather at times the two registered images may be represented separately, e.g. side-by-side. The important result of the act of registering is that manipulation made on one of the images will effect the other as well.

In the following, the invention will be described with particular reference to an embodiment in which the first image is a cephalometric image and the second image is a virtual three-dimensional image. This specific reference should not however be construed as meaning that the invention is limited thereto. On the contrary, by applying the general teaching of the invention, information may be transferred between images obtained by other imaging techniques.

In accordance with one embodiment of the invention, after landmarks have been defined in the three-dimensional virtual images and in the cephalometric image, the correct orientation of the virtual three-dimensional teeth model has to be determined so as to allow it to be brought into conformity with the cephalometric image. This may at times require extensive computational time. It has however been found that the process of registration of the two images can be considerably accelerated by defining the cephalometric image to overlap the mid palatal plane of the virtual three-dimensional teeth image. In other words, the cephalometric image is defined to lie on the mid palatal plane and the cephalographic image is then adjusted until the basic landmarks overlap with the projection of the corresponding basic landmarks of the virtual three-dimensional image onto the mid palatal plane.

The invention permits also an analysis of the effect of teeth displacement on various aspects of the cranofacial complex. For example teeth may be displaced on the virtual three-dimensional image of teeth model in a manner they are expected to be shifted during the course of the orthodontic treatment. Thus, for example, by marking various landmarks on a displaced teeth and marking and then displacing the same landmarks in the cephalometric model, it may be possible to check on both images whether the orthodontic treatment achieves a result which matches a certain acceptable norm or how changes should be made to achieve such a norm. If, for example, a desired result as viewed in an amended cephalometric image (namely a cephalometric image after a tooth has been displaced) does not match the desired results, it is possible to go back to the virtual three-dimensional teeth model and proceed with a simulation and then map the results onto the cephalometric image, and so forth.

By way of example, in order to achieve the same degree of displacement in one image, the shifting of a certain landmark which is associated with a displaced object is then compared to some basic landmarks and the same relation of displacements is then related to the other image.

One particular example of analysis which can be made by such simulation is to determine the effect of such displacement on soft facial tissue, particularly outer facial tissue. This will allow an estimation of the effect of the orthodontic treatment on the esthetic appearance of the individual.

A simulation of the treatment and then translation of the results to a cephalometric image allows also to determine whether shifts in various elements such as the jaw, are within permitted physiological or aesthetical limits. An uncontrolled shifting of a tooth or a jaw in an orthodontic treatment may give rise to various physiological and functional problems.

The invention will now be illustrated below with reference to some specific, non-limiting embodiments, with occasional reference to the accompanying drawings.

BRIEF DESCRIPTION OF THE DRAWINGS

FIG. 7A shows the user's interaction modules whereas FIG. 7B shows the software functionality underlying the manner of performing of displacement and mapping the displacement from the three-dimensional virtual teeth model to the cephalometric image.

FIG. 8A shows the user's interaction modules whereas FIGS. 8B shows the software functionality underlying the manner of performing of displacement and mapping the displacement from the cephalometric image to the virtual three-dimensional teeth model.

DETAILED DESCRIPTION OF SPECIFIC EMBODIMENTS

In accordance with the present invention images are acquired including at least one two-dimensional teeth image and at least one three-dimensional teeth image and both are combined for the purpose of improving the orthodont's ability to predict the effect of orthodontic treatment on various parameters. This combination allows the orthodont to considerably increase the depth of his understanding on the outcome of the orthodontic treatment. Hitherto, analysis which was made on a cephalometric images could not have been readily translated to the other tools available to him—this being the three-dimensional teeth model, typically a plaster model. In the reverse, information gained by him from studying a three-dimensional teeth model, could not have been readily translated to a cephalometric image. As is well known to the artisan, each one of the images allows a limited range of analysis which can be made and a true analysis can only be gained from thorough analysis based on the two types of images.

It is only with the present invention that a proper analysis becomes feasible.

An image, once acquired and converted to a representation within a computer environment can be manipulated, e.g. by displacing certain elements, such as one or more teeth or even an entire jaw. The cepthalometric image allows to view the, interrelation between some elements and may be used, for example, to test the effect of the treatment on some physiological or functional parameters as well as the aesthetic parameters. There is, however, a significant deficiency in that it is impossible to fully translate this information to the three-dimensional real-life environment. The present invention permits a proper analysis of the effect of displacement of elements and or better understanding of how changes will effect the real-life situation.

Figure 1A:
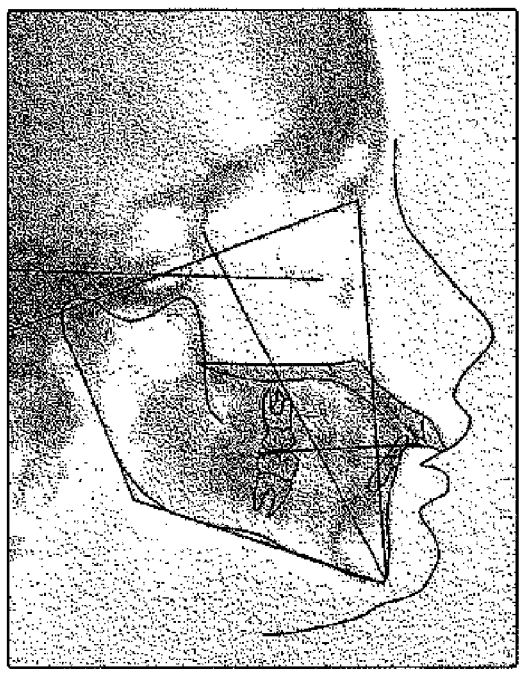
FIG. 1A shows an example of a radiographic cephalometric image.
Figure 1B:
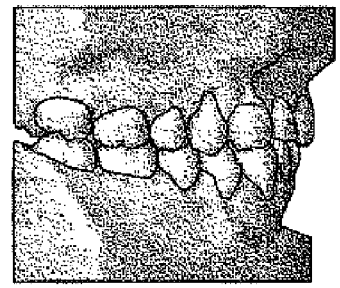
FIG. 1B shows a virtual three-dimensional image of teeth, presented in the manner resembling a plaster teeth model.

Reference is first being made to FIGS. 1A and 1B, showing respectively, a cephalometric radiograph and a three-dimensional virtual teeth image. The virtual teeth image which is shown in FIG. 1B, is represented in a manner resembling a plaster teeth model. As will no doubt be appreciated by the artisan, this is but an example, and the two-dimensional or the virtual three dimensional teeth image may be represented in a different way.

Figure 2:
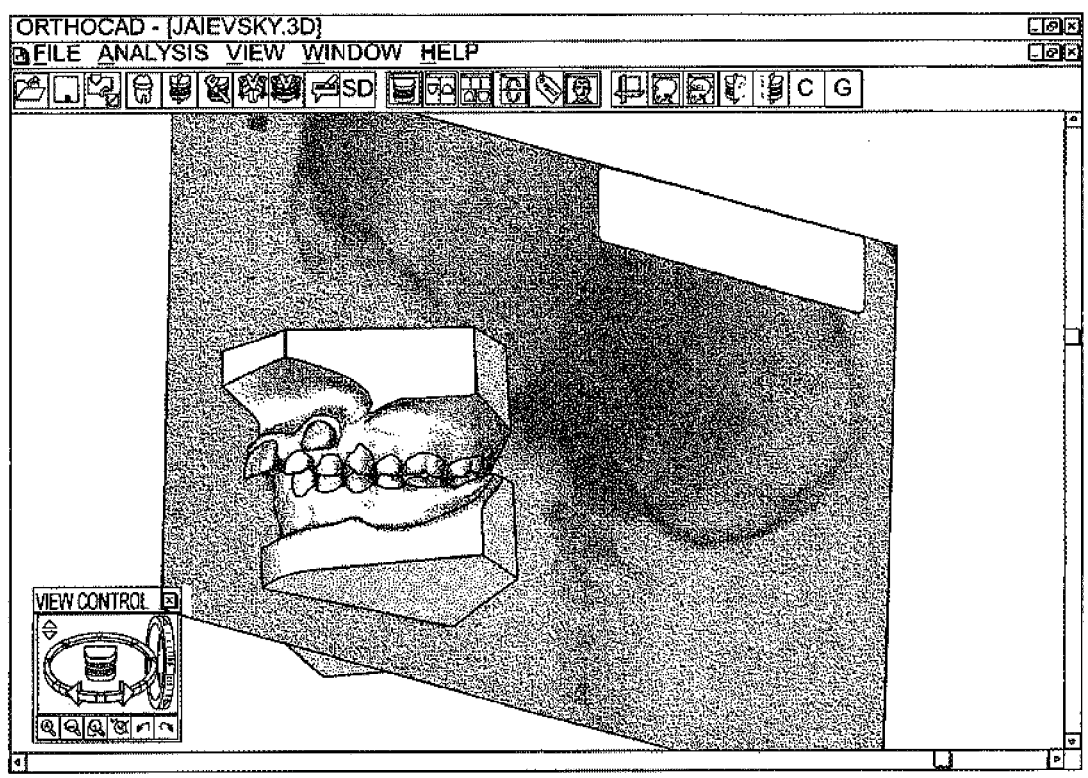
FIG. 2 shows a super-position of a three-dimensional teeth model and a cephalometric image.

Prior to the present invention, each of these different images, was represented separately. The three-dimensional virtual image was represented either as a plaster model or a three-dimensional virtual representation in a computer environement. In accordance with the invention, two different images, one being a two-dimensional image. e.g. a cephalometric radiograph, is combined with a three-dimensional teeth image. A super-position of two such images is represented in exemplary FIG. 2. As can be seen, the cephalometric image is combined with the three-dimensional virtual teeth image such that it lies on the mid palatal plane of the three-dimensional virtual teeth image. The relative position of the two images is fixed such that basic landmarks defined in the two images concur, as will be described farther below.

Figure 3:
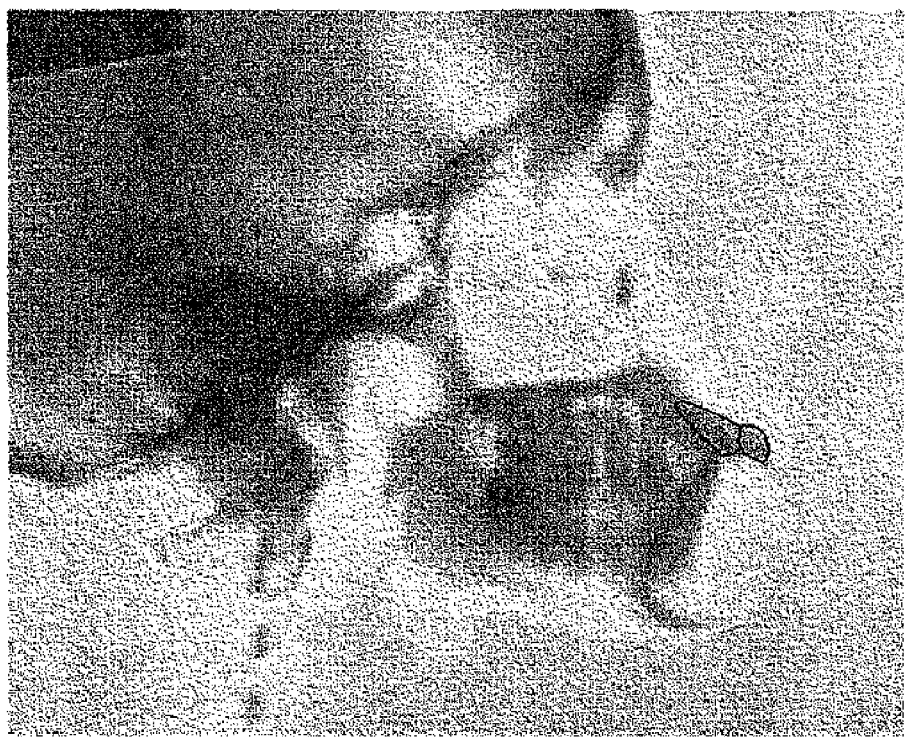
FIGS. 3A and 3B show two examples of super-position of a three-dimensional model and a video cephalometric image.
Figure 3A:
Figure 3B:
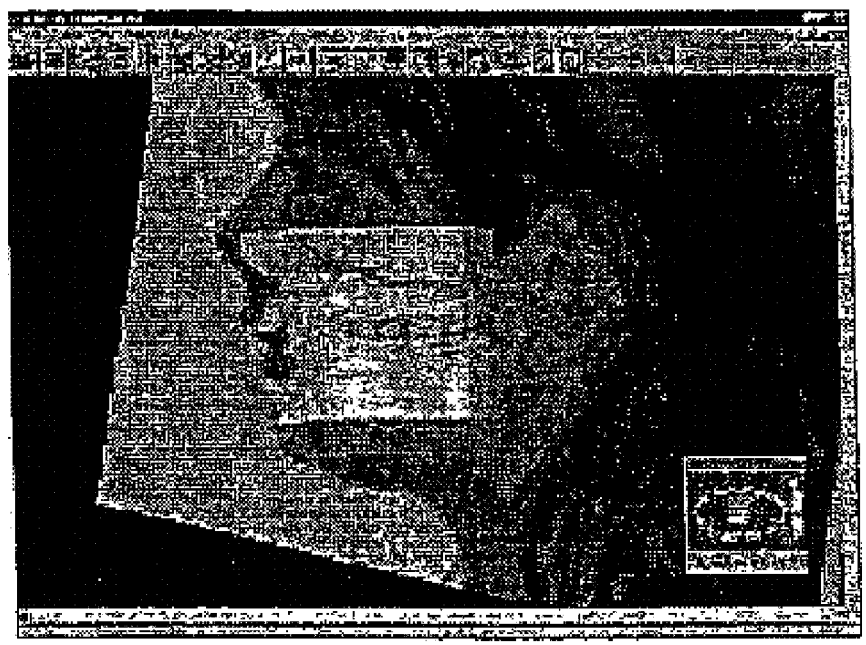

Another implementation of the invention can be seen in exemplary FIGS. 3A and 3B. In these figures, a three-dimensional virtual teeth image is superpositioned with a lateral or profile picture of an individual. The profile pictures in FIGS. 3A and 3B are each from a slightly differently orientation and accordingly the virtual three-dimensional teeth model in FIG. 3B is rotated with respect to the orientation it of the model in FIG. 3A.

In order to combine a cephalometric image and a three-dimensional virtual model, basic landmarks have to be defined and marked in both images. These basic landmarks may be entered manually by the user, although alternatively, they may be automatically generated by a computer, based on standard image analysis method, or based on an earlier user input. Generally, such basic landmarks may be arbitrary landmarks or may be orthodontic relevant landmarks which may be used later in a cephalometric analysis, in accordance with one of the acceptable norms therefor. (For review on a cephalometric analysis see Radiographic Cephalometry, From Basics to Videoimaging, Jacobson A., et al., Quintessence Publishing Co., Inc., Chicago, Berlin, 1995).

Figure 4:
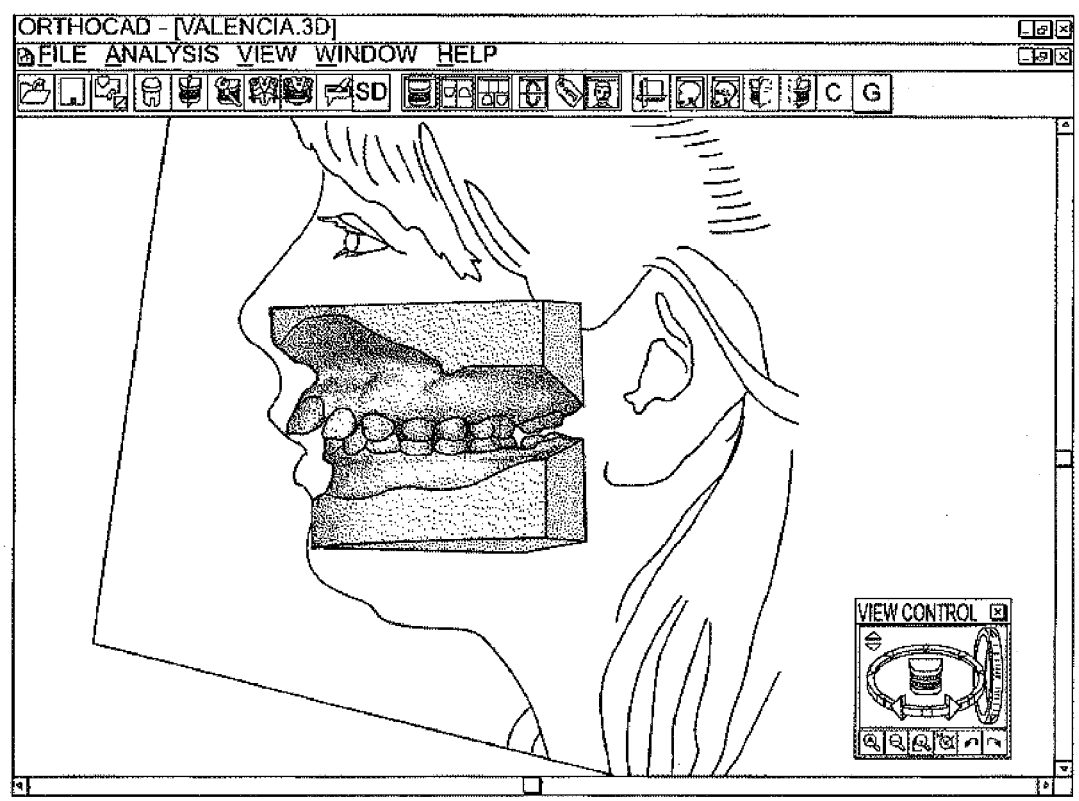
FIG. 4A shows a cephalometric image with some basic landmarks marked thereon.
FIG. 4B shows a three-dimensional virtual image of the same teeth as those shown in the cephalometric image of FIG. 4A, with the same basic landmarks marked thereon.
Figure 4A:
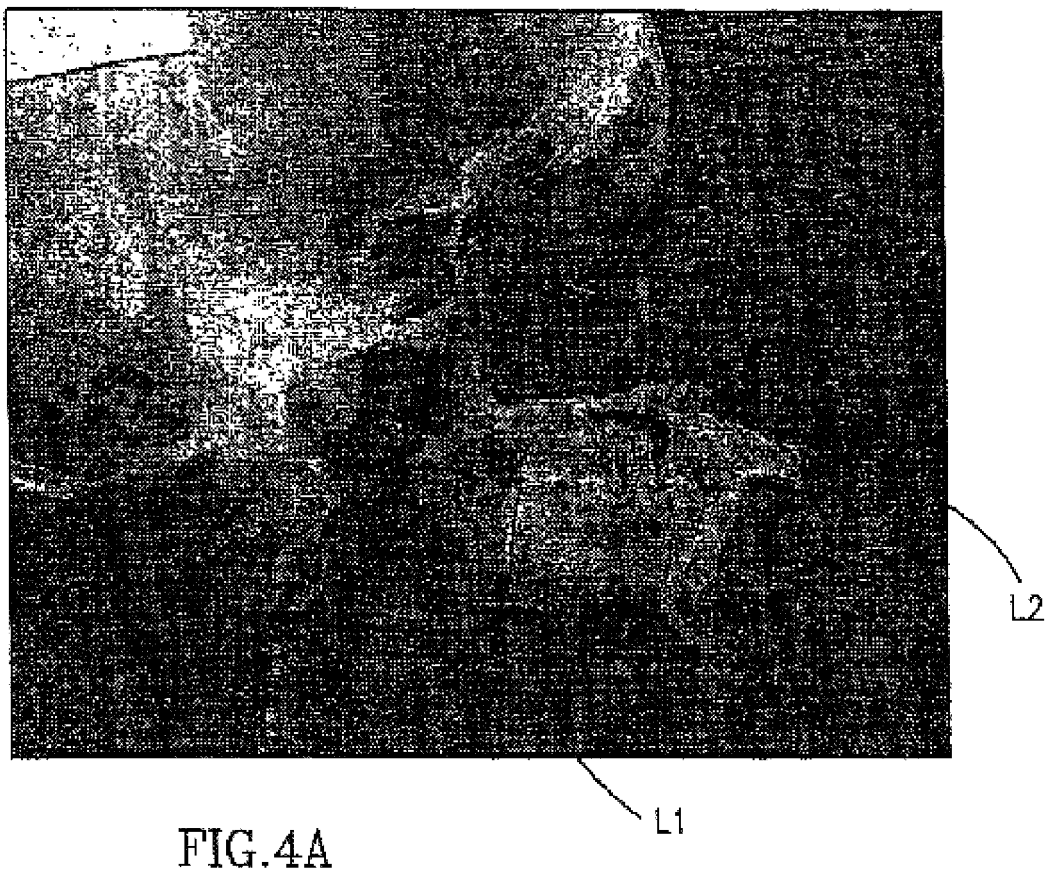
Figure 4B:
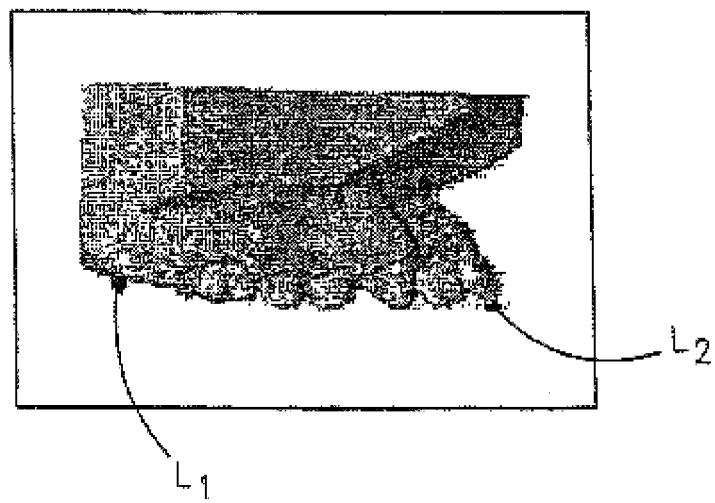
Figure 5:
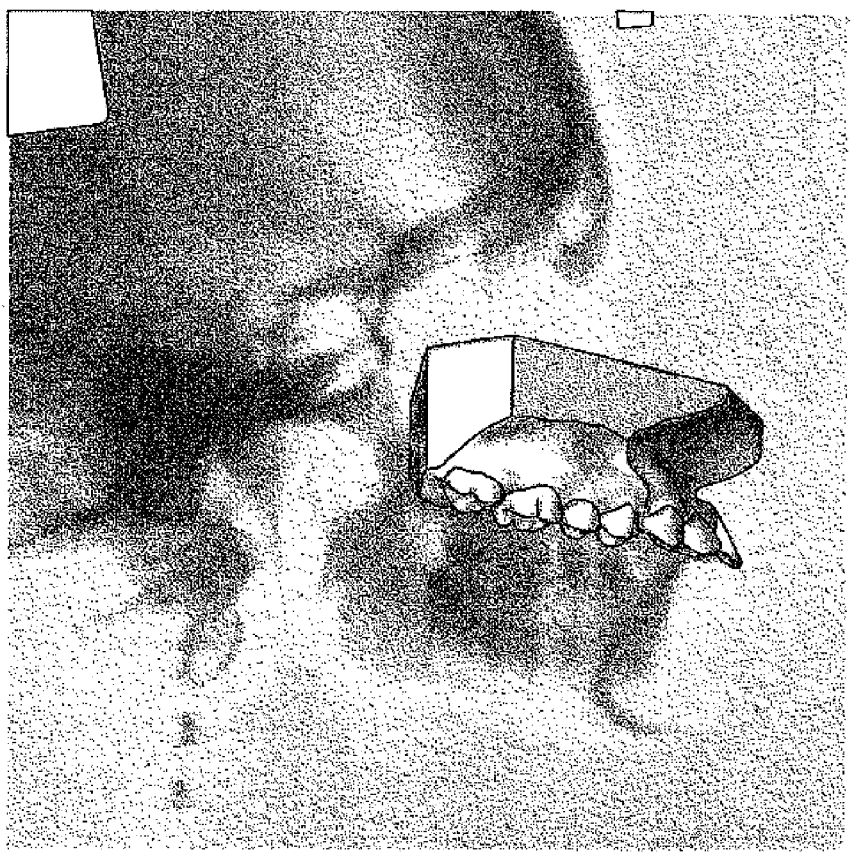
FIG. 5 shows a super-position of the two images.

A cephalometric radiograph and the three-dimensional teeth model from the same individual, are shown in FIGS. 4A and 4B. In these figures, two basic landmarks have been marked—L1 and L2. After these landmarks have been marked, the two images are brought into registration which results in super-positioning as can be seen in FIG. 5 (the same two landmarks L1 and L2 can also be seen here). The registration in the manner shown in FIGS. 4A, 4B and 5 is performed using two defined landmarks. Obviously, it is possible at times to use more landmarks for this purpose to increase accuracy of registration.

In order to reduce computational time, the cephalometric radiograph is combined with the three-dimensional virtual teeth image by placing (in a virtual sense) the cephalometric image on the mid palatal plane. For proper registration, the scale of the two images has to be adjusted and then one image has to be shifted versus the other until the projection of the basic landmarks of the three-dimensional virtual image of teeth model onto its mid palatal plane are in register with the corresponding landmarks in the cephalometric image.

The cephalometric radiograph and the cephalometric videograph as shown herein, are images as acquired by the utilized imaging technique. It should however be noted that at times it is advantageous to produce initially a representation of the image, e.g. a graphic representation of boundaries of objects of interest within the image. For example, rather than a full cephalographic image, a representation comprising boundaries of some major bones and several teeth, e.g. the first and second molar teeth and the incisors. These aforementioned teeth are usually the important teeth for the cephalometric analysis, as their position is relatively sensitive to displacement of teeth and jaws. Furthermore, the position of these teeth is an important marker for studying or gauging the effect of teeth position on various functional as well as aesthetical facial aspects.

Producing a graphical representation of some aspects of an image, particularly of a cephalometric image, is very useful for the purpose of a virtual displacement of the teeth in the image so as to study the effect of the treatment on functional or facial aesthetic parameters, as generally known per se.

Figure 6:
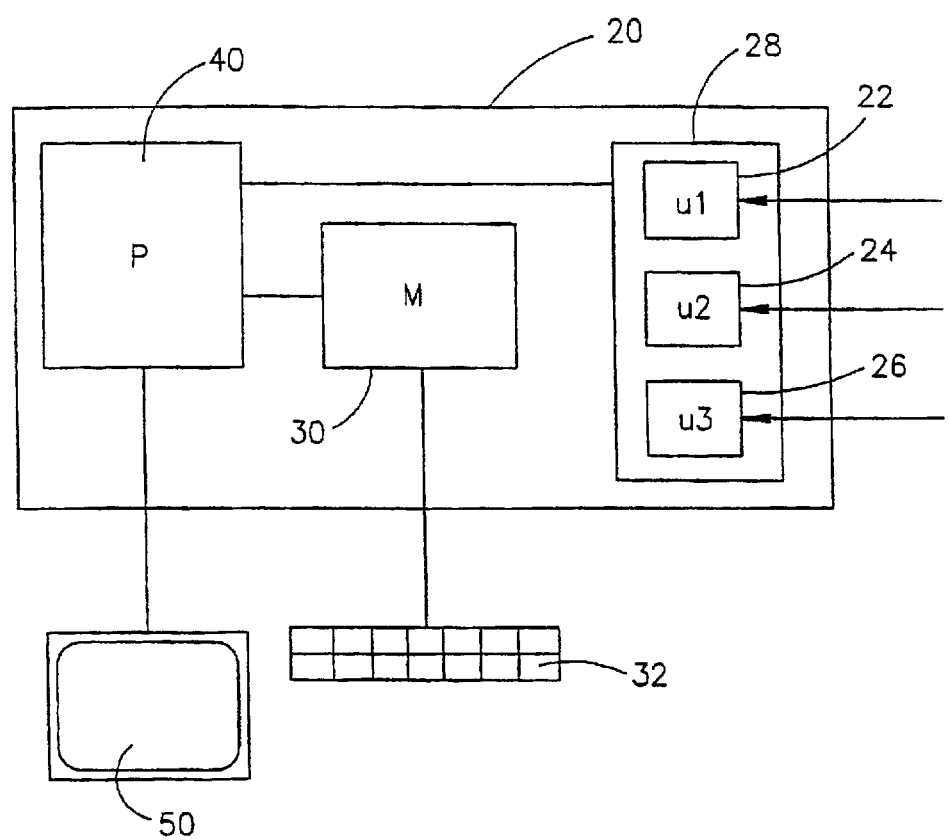
FIG. 6 is a block diagram representation of a system in accordance with the invention.

A system in accordance with the embodiment of the invention can be seen in FIG. 6. It comprises a central computing unit 20 with three input utilities 22, 24 and 26, which may be integral within module 28. These utilities may comprise, as known per se, a data entry port and the necessary data transfer software. Furthermore, rather than importing of data through a data entry port, the data to these utilities may be imported from a storage media or from an information carrier. e.g. a magnetic or an optical disk. As will no doubt be further understood, module 28 may also comprise a scanner for scanning images, may comprise a camera for direct image acquisition, etc.

The system still further comprises a module 30, connected to a user input interface 32 e.g. a keypad, a cursor driver, etc. By means of interface 32 the user may define the landmarks or may induce the system to enter into various operational modes, some of which will be explained below.

Module 30 and utility 28 are connected to a processor 40 for image processing so as to combine the two images as described, for example further below. Processor 40 may be connected to monitor 50 and may be also connected to other display means, e.g. a printer.

Figure 7A:
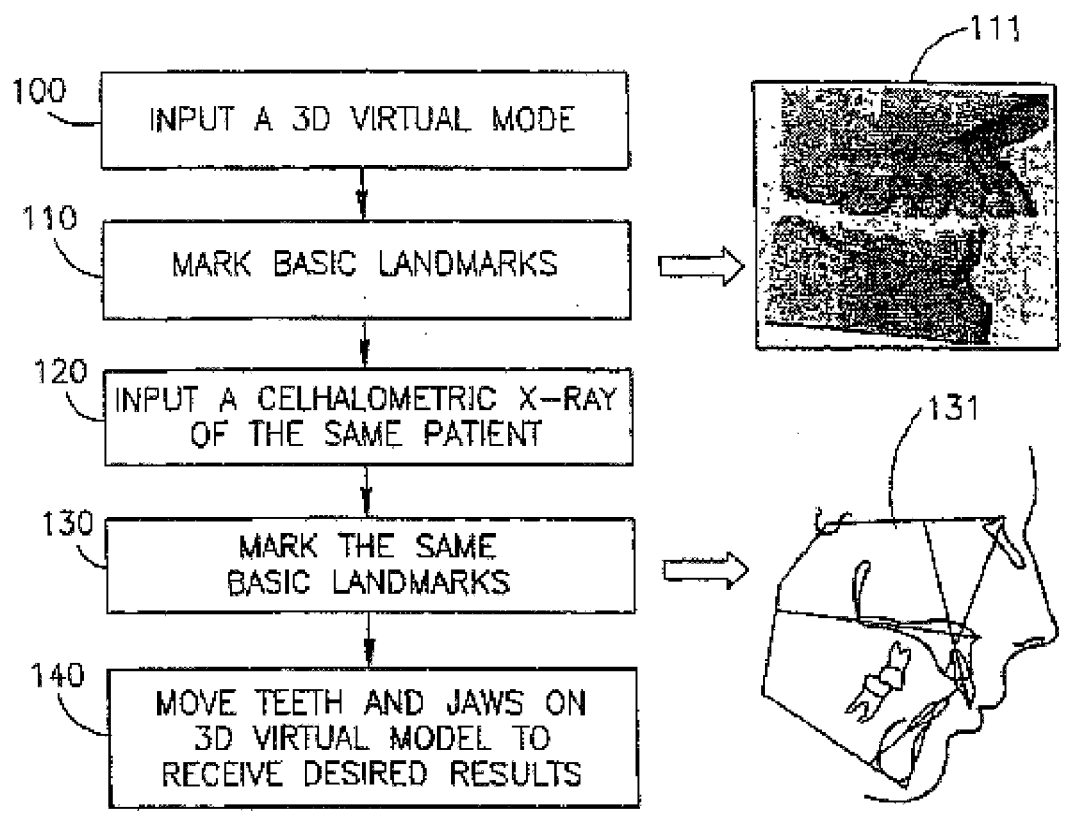
FIGS. 7A and 7B are flowcharts showing the manner of mapping elements from a three-dimensional virtual teeth model to a cephalometric image.
Figure 7B:
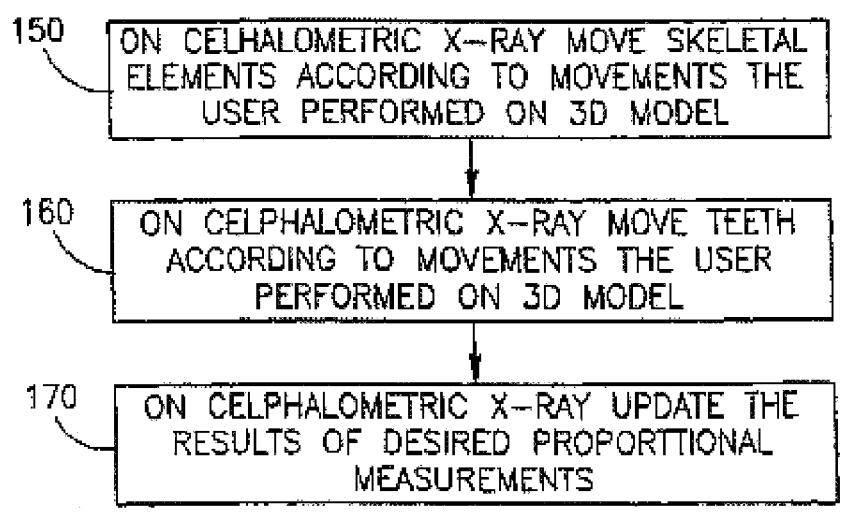

A flowchart of an embodiment of the manner of linking between a three-dimensional virtual teeth model and a cephalometric image can be seen in FIGS. 7A and 7B. FIG. 7A is a flowchart of the user interaction steps whereas FIG. 7B is a software functionality flowchart on the manner of combining the two images. At a first step 100, the system receives an input of data representative of a three-dimensional virtual teeth model. Then at 110, basic landmarks are marked on discernable objects in the three-dimensional virtual teeth model as represented in image 111. Such basic landmarks may, for example, be points on crowns and roots of upper and lower first molars (landmarks 1–4 of image 111) as well as on crowns and roots of upper and lower centrals (landmarks 5–8 in image 111). Landsmarks 1 and 4 as well as landmarks 5 and 8 mark the approximate position of the roots of the teeth. The real root position cannot be seen in such a model but the orthodont, based on his experience, can relatively accurately mark their roots' position.

At a next step 120, a cephalometric image of the same patient is input and on this image, the same key points are then marked (see 131). Then, the two images may be matched, which may be by way of super-position as shown above, which can be represented on a screen, or by any other way of mapping of each location in one image to that of the other image.

At a next step 140 teeth and jaws in the three-dimensional model may be displaced on the three-dimensional model to receive a desired result. Then, as represented in the flowchart of FIG. 7B, the software at next steps 150 and 160 moves skeletal elements and teeth, respectively, according to movement performed by the user on the three-dimensional virtual teeth model. Then, at 170, a cephalometric analysis can be made on the amended (after displacement) cepthalometric image to see whether desired proportional measurements have been reached in such teeth displacement or whether any medication should be made.

Figure 8A:
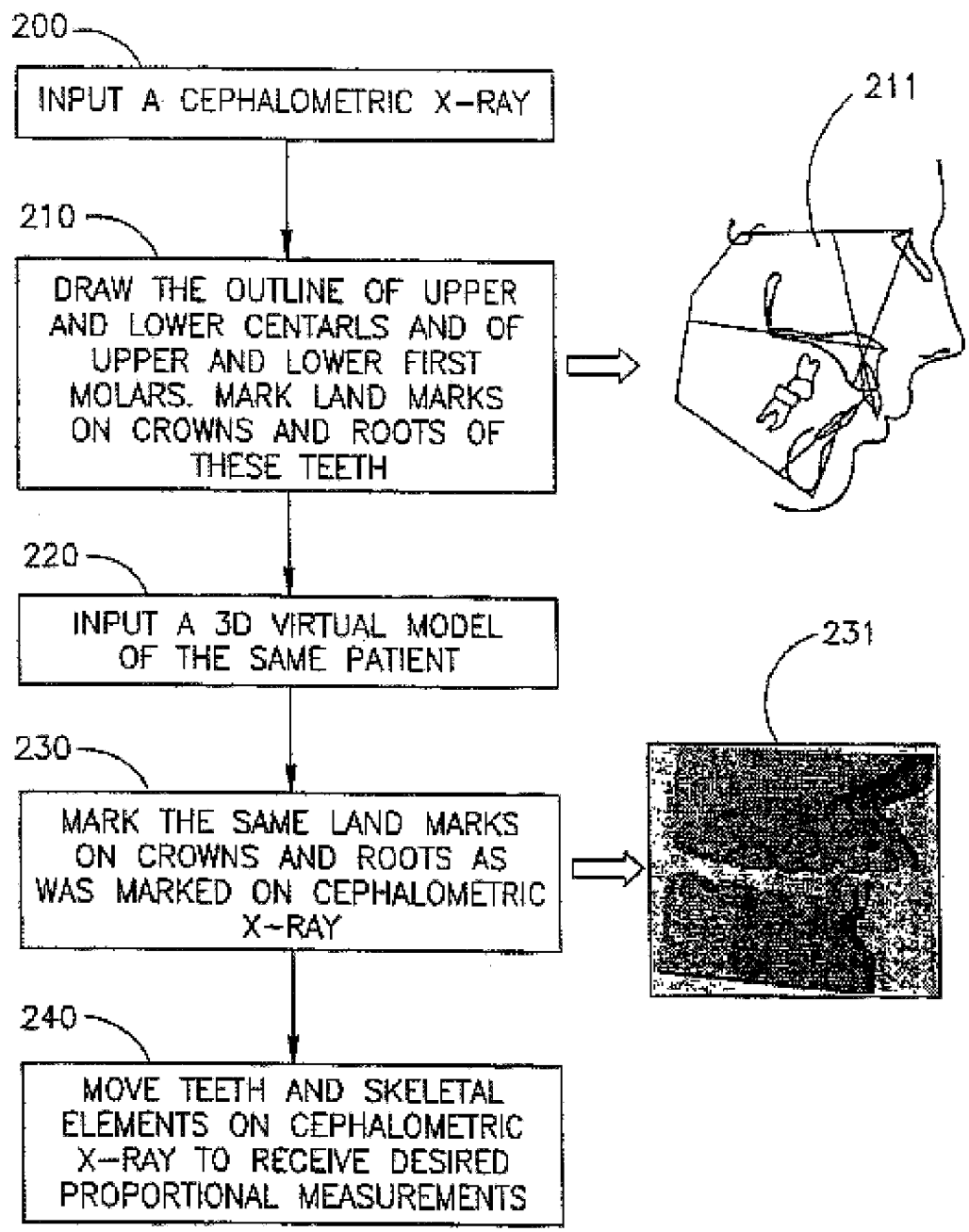
FIGS. 8A and 8B are flowcharts showing the manner of mapping elements from a cepthalometric image to a three-dimensional virtual teeth model.
Figure 8B:
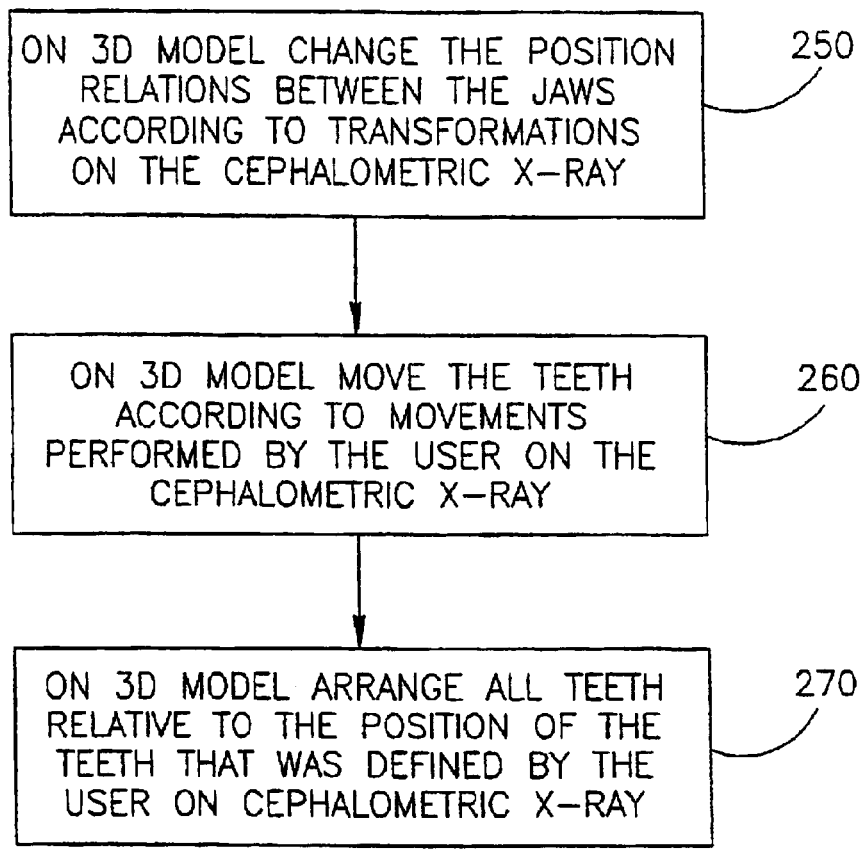
Figure 1A:
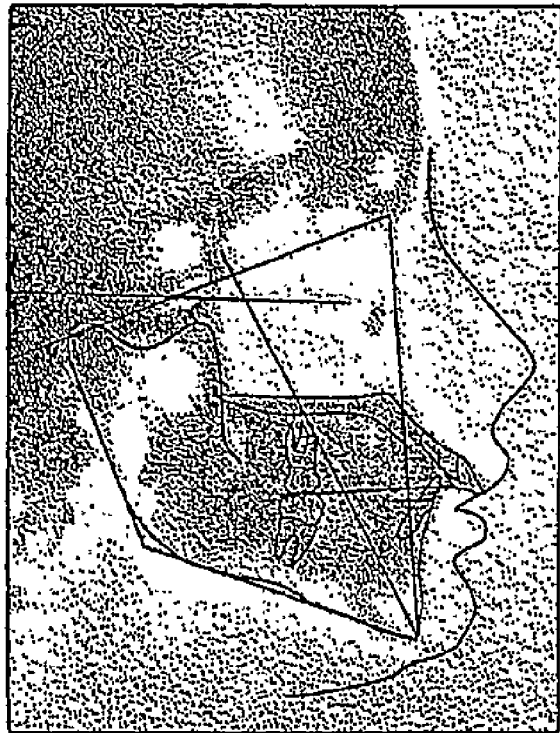
Figure 1B:
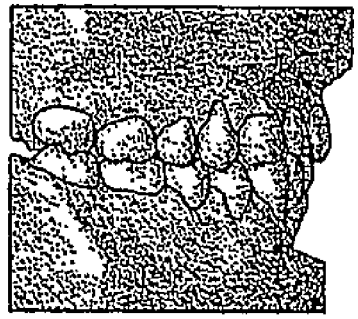
Figure 2:
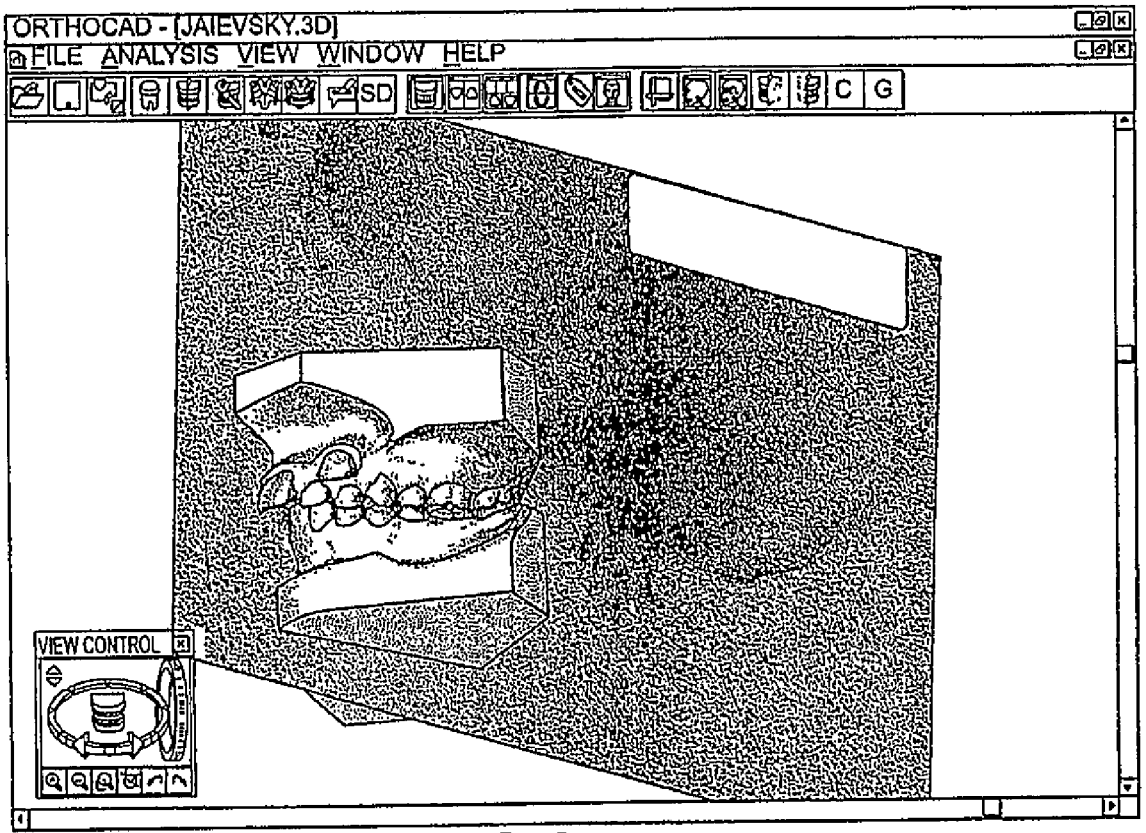
Figure 3A:
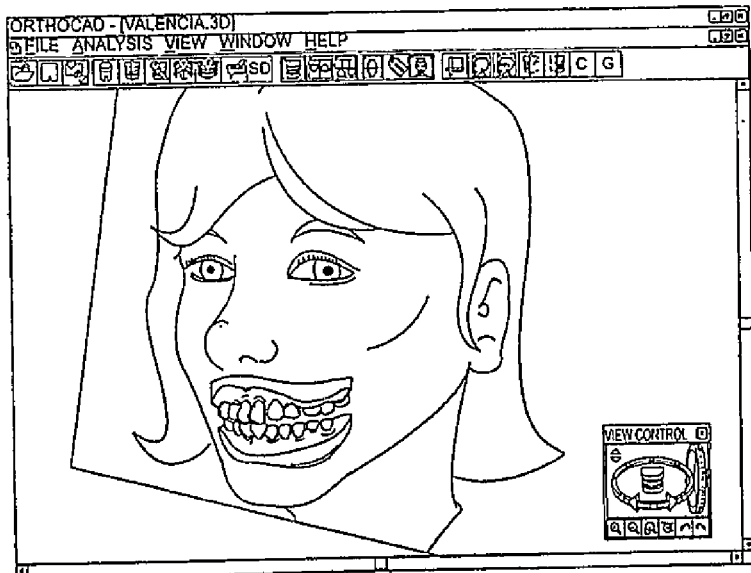
Figure 3B:
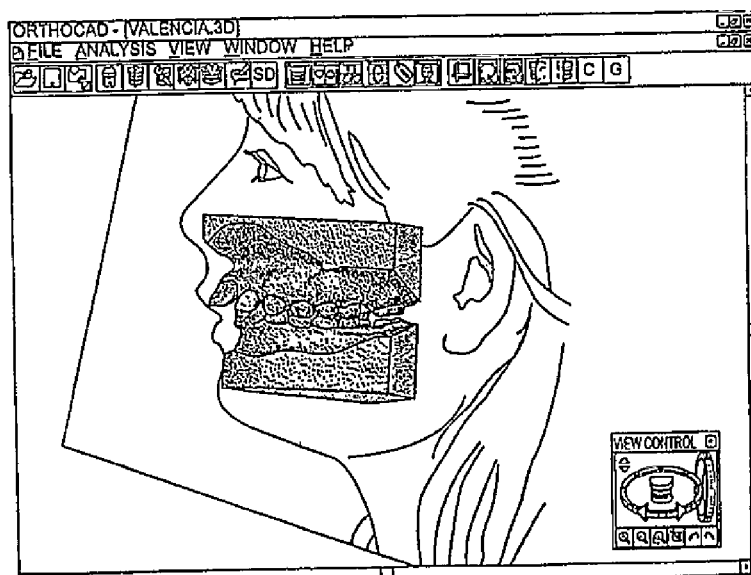
Figure 4A:
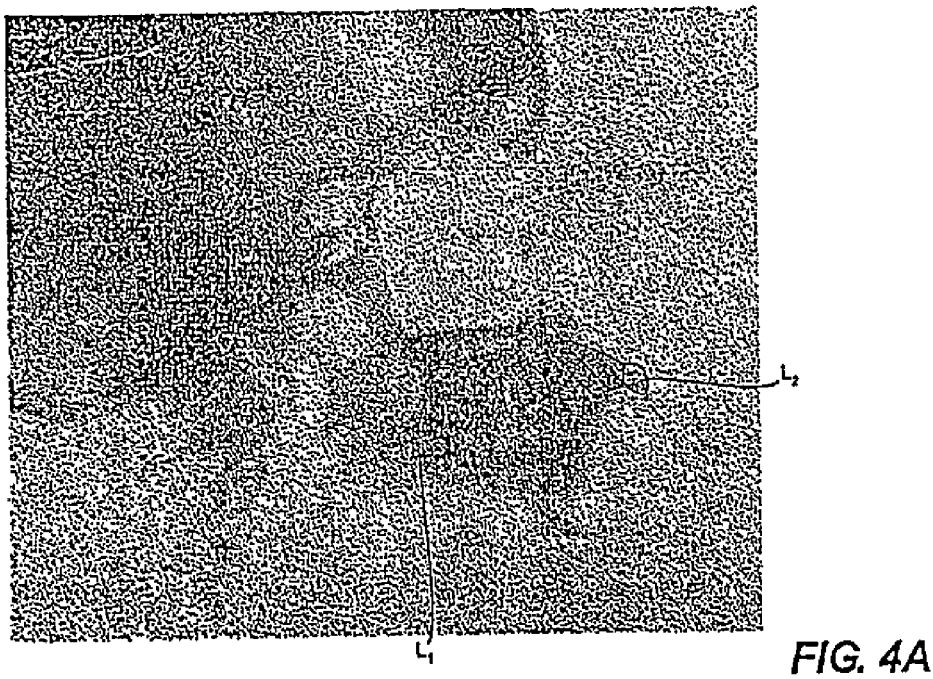
Figure 4B:
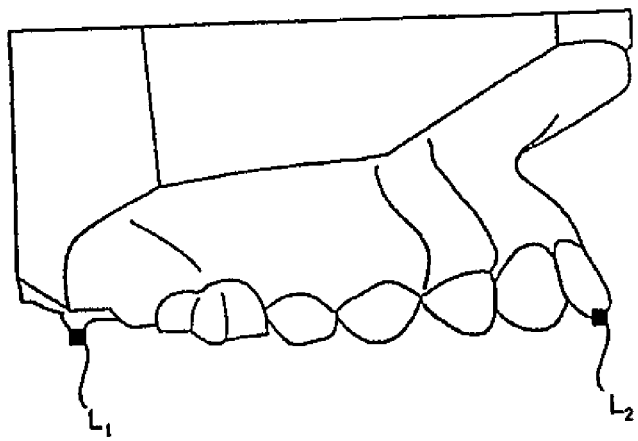
Figure 5:
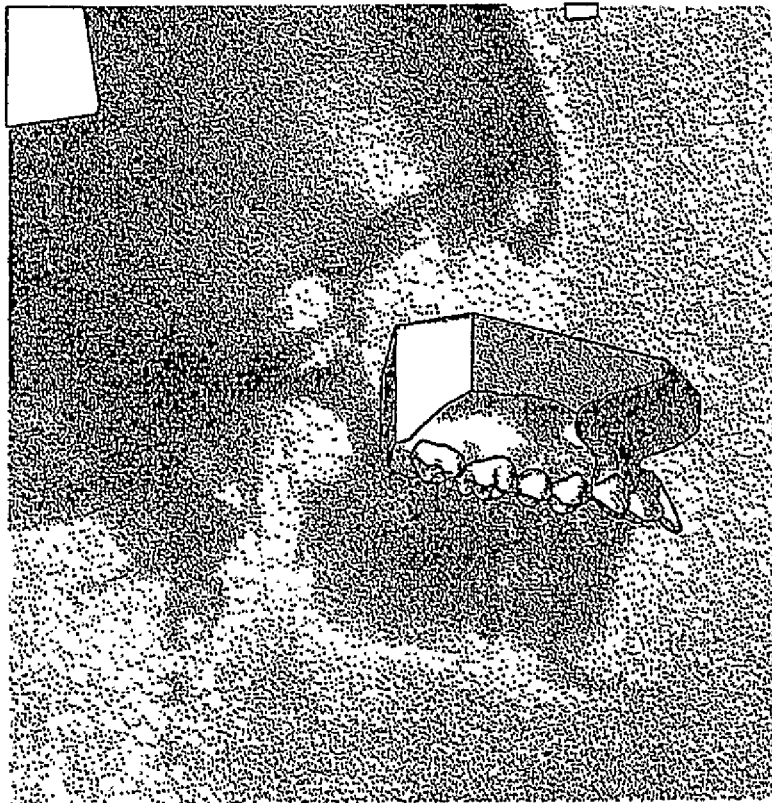
Figure 6:
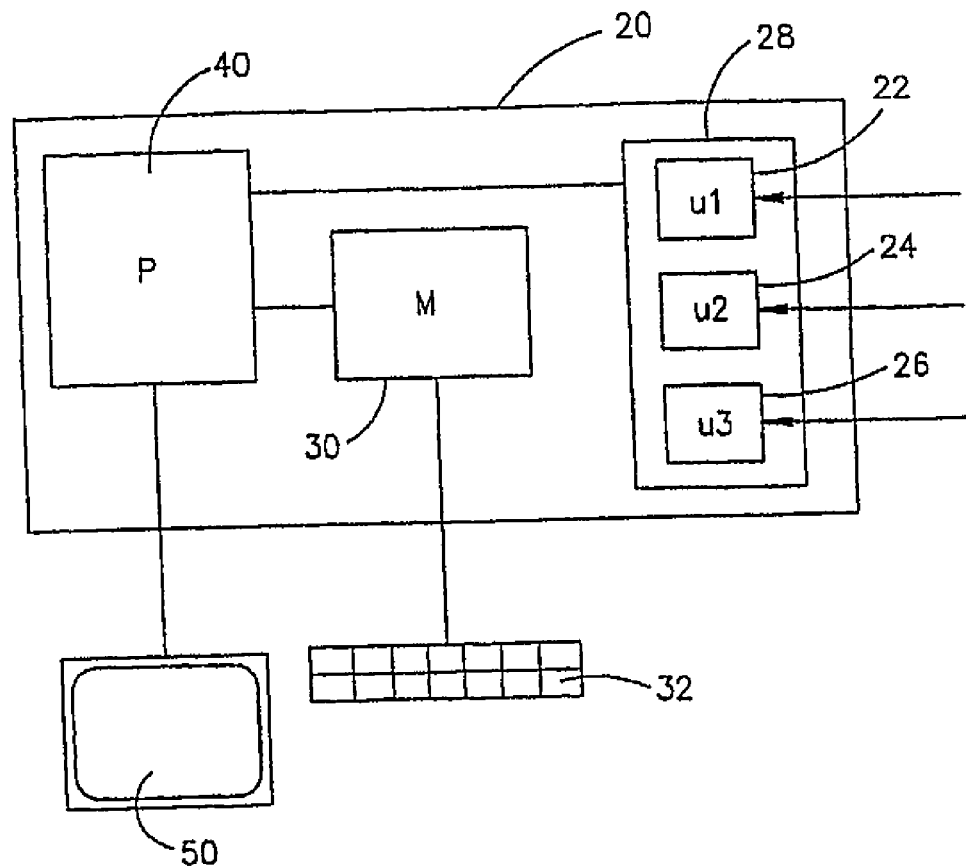
Figure 7A:
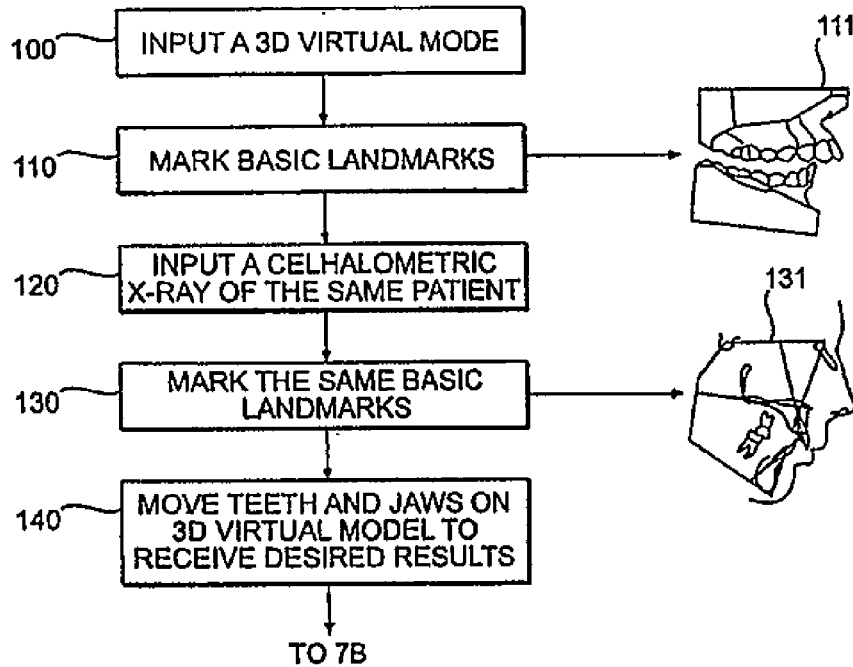
Figure 7B:
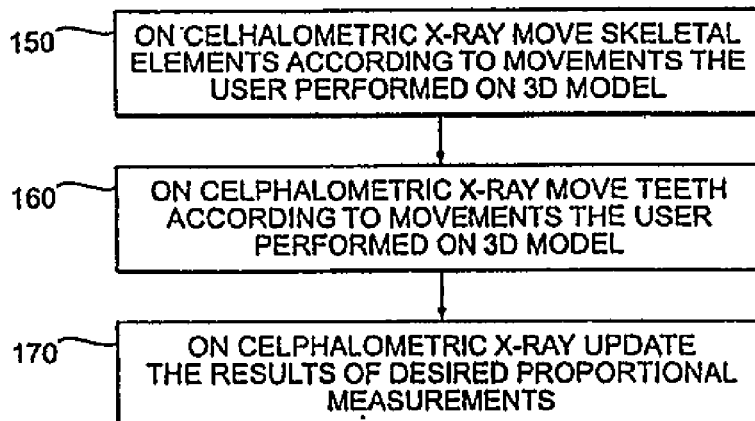
Figure 8A:
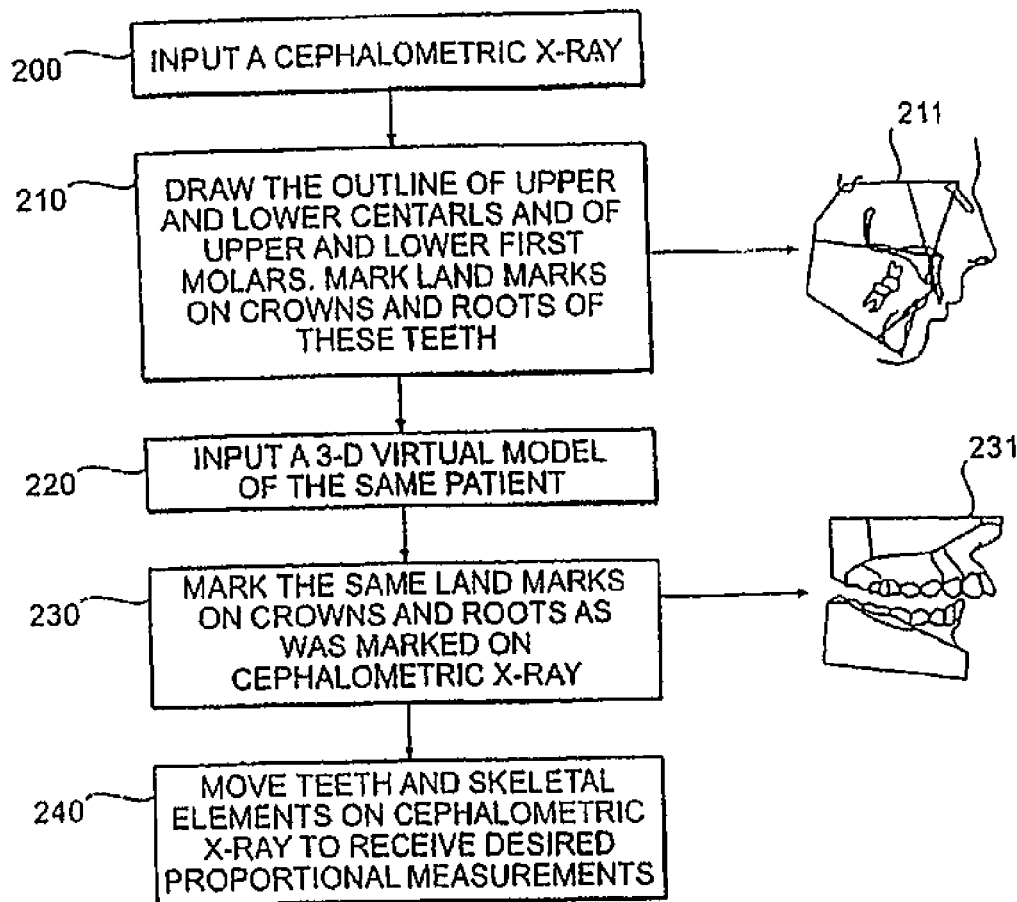
Figure 8B:
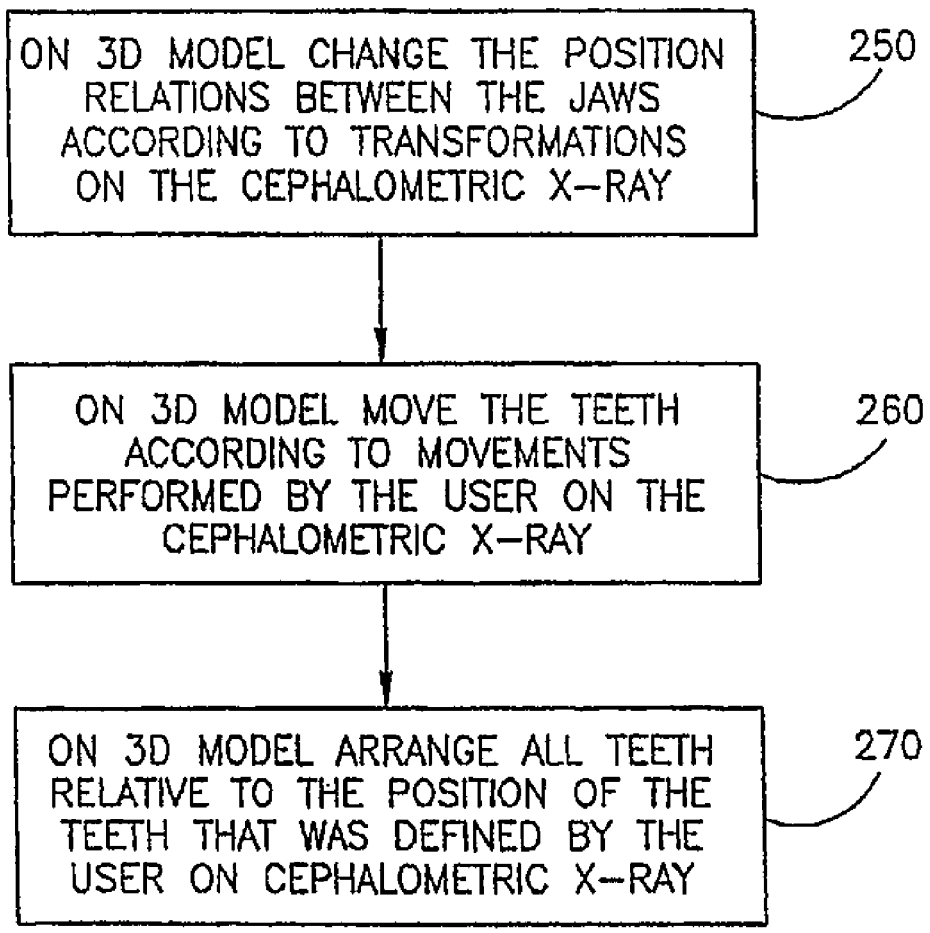
Figure 1A:
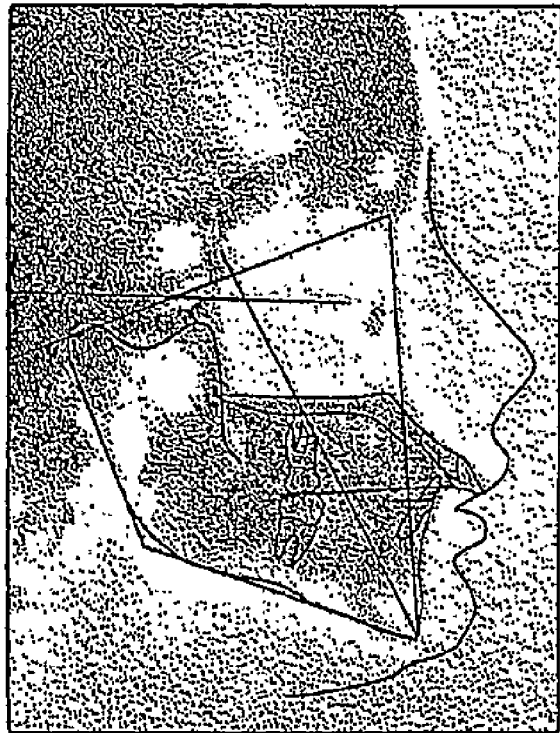
Figure 1B:
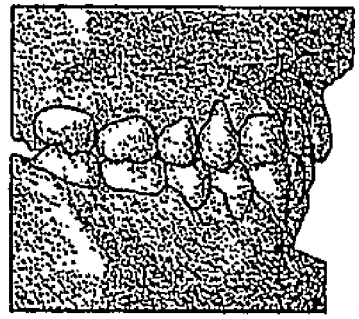
Figure 2:
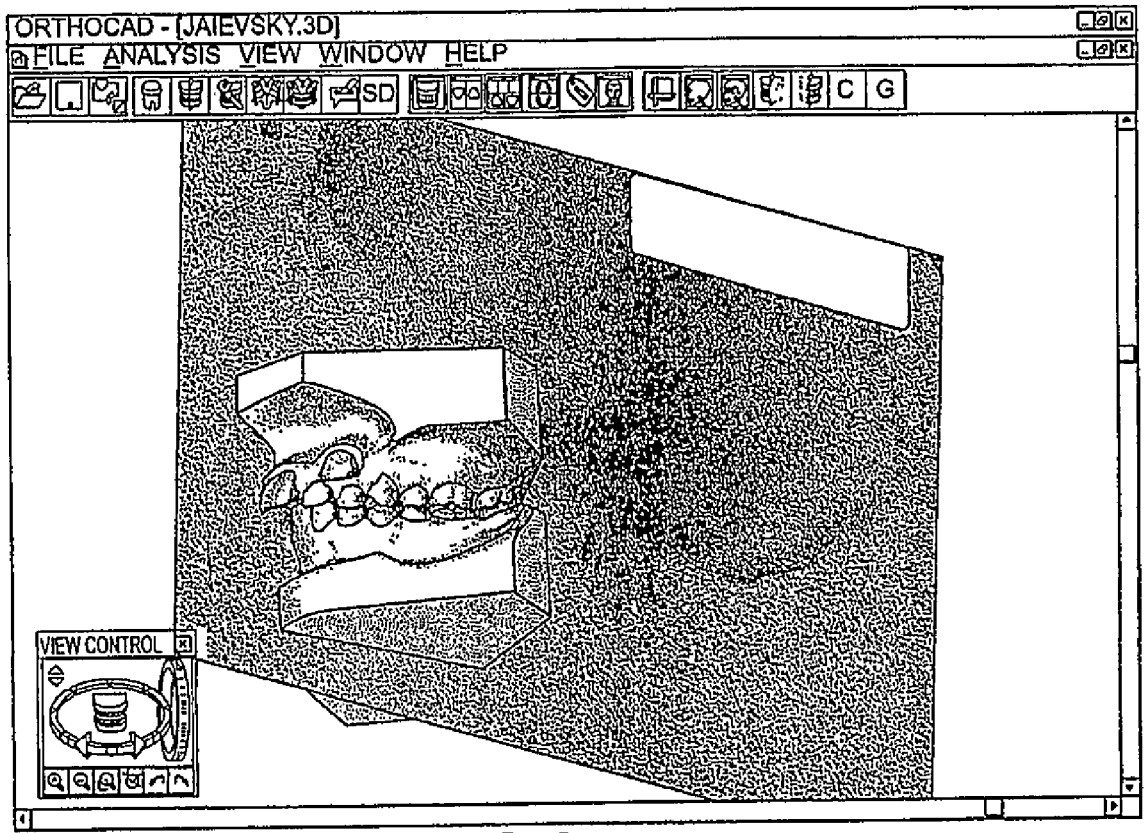
Figure 3A:
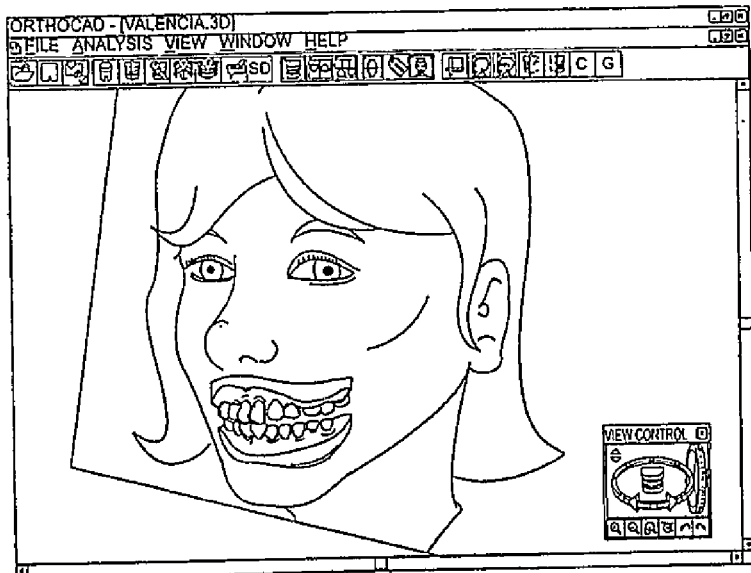
Figure 3B:
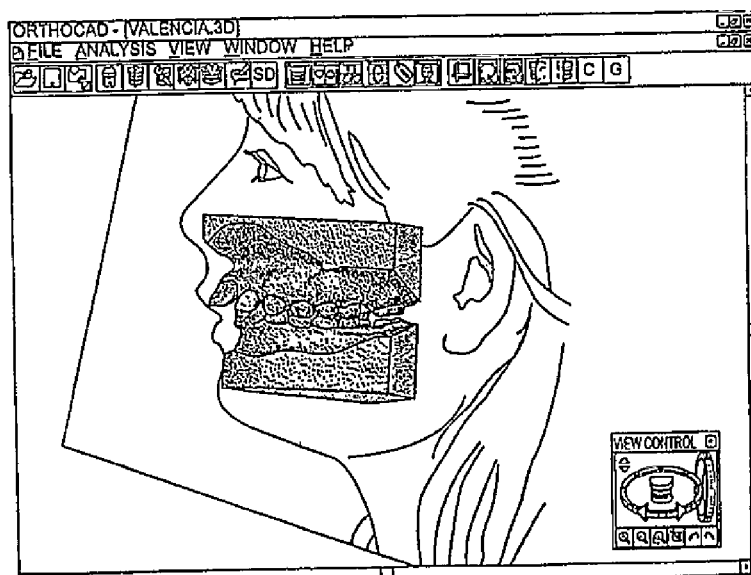
Figure 4A:
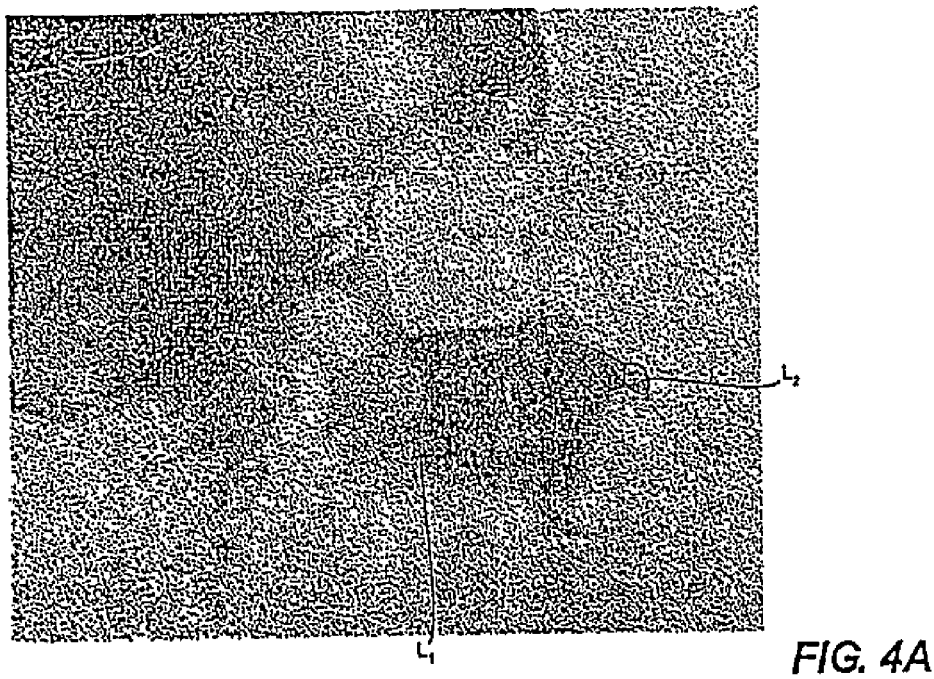
Figure 4B:
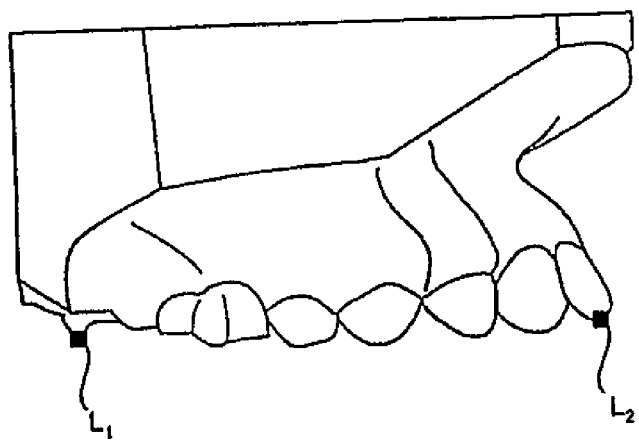
Figure 5:
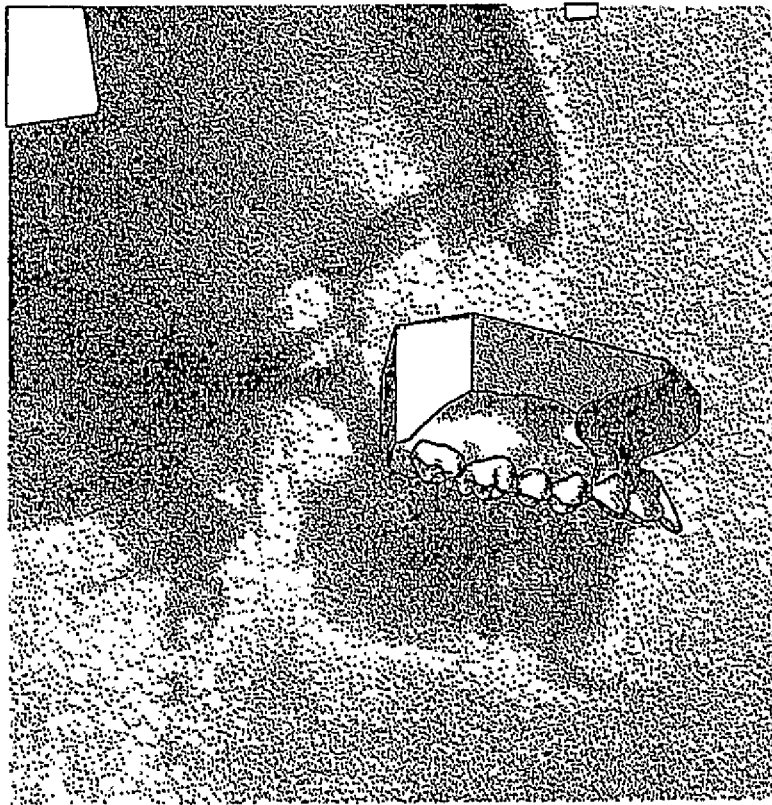
Figure 6:
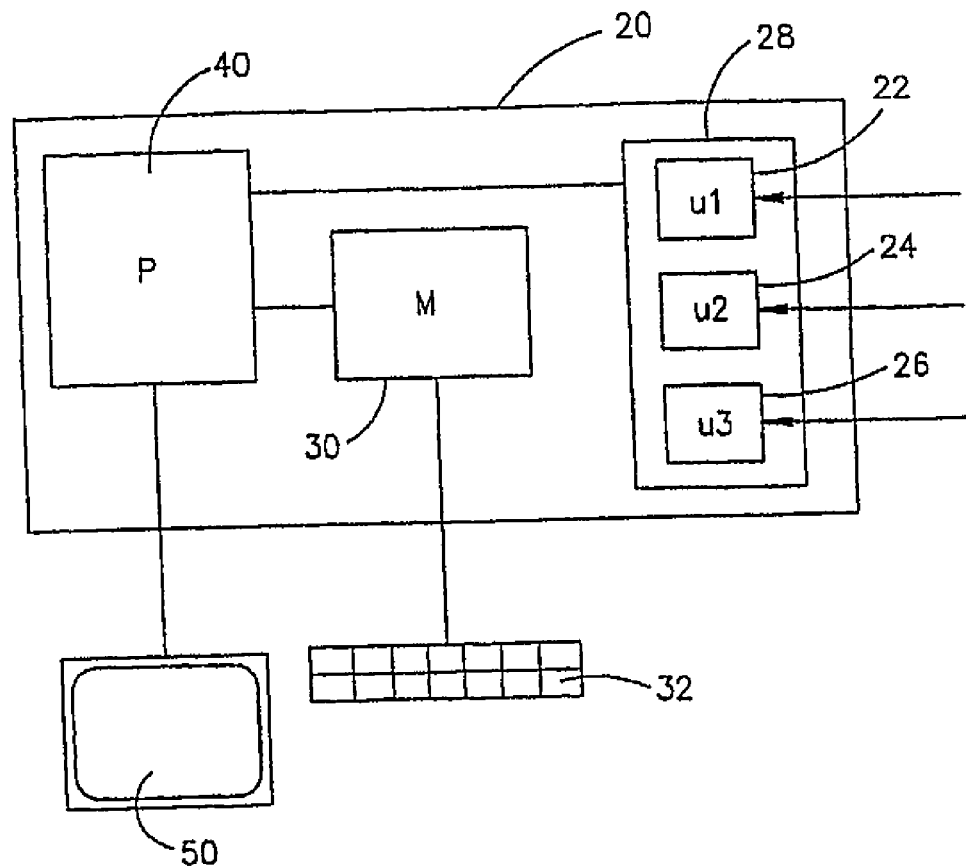
Figure 7A:
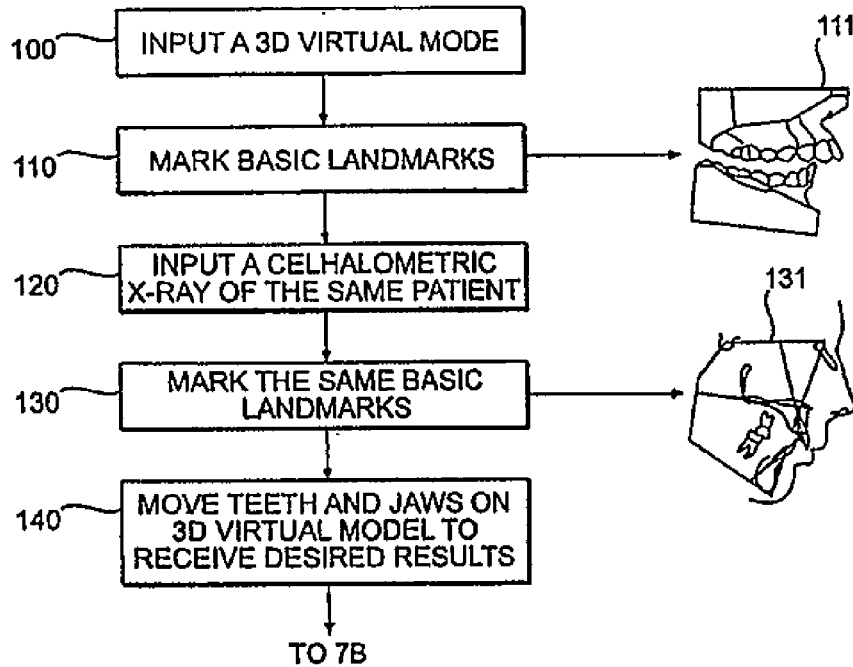
Figure 7B:
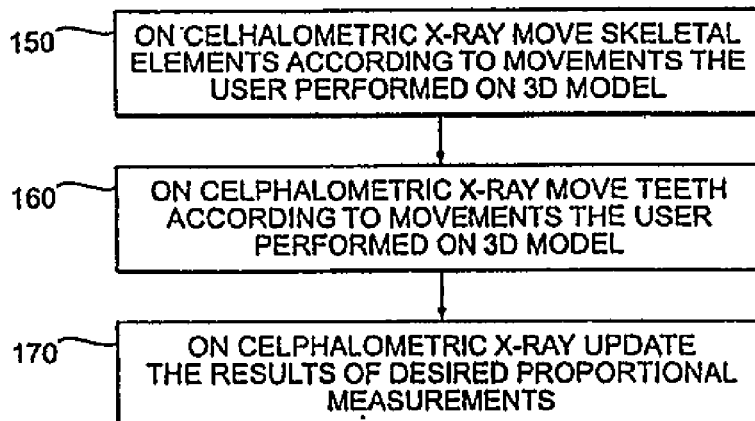
Figure 8A:
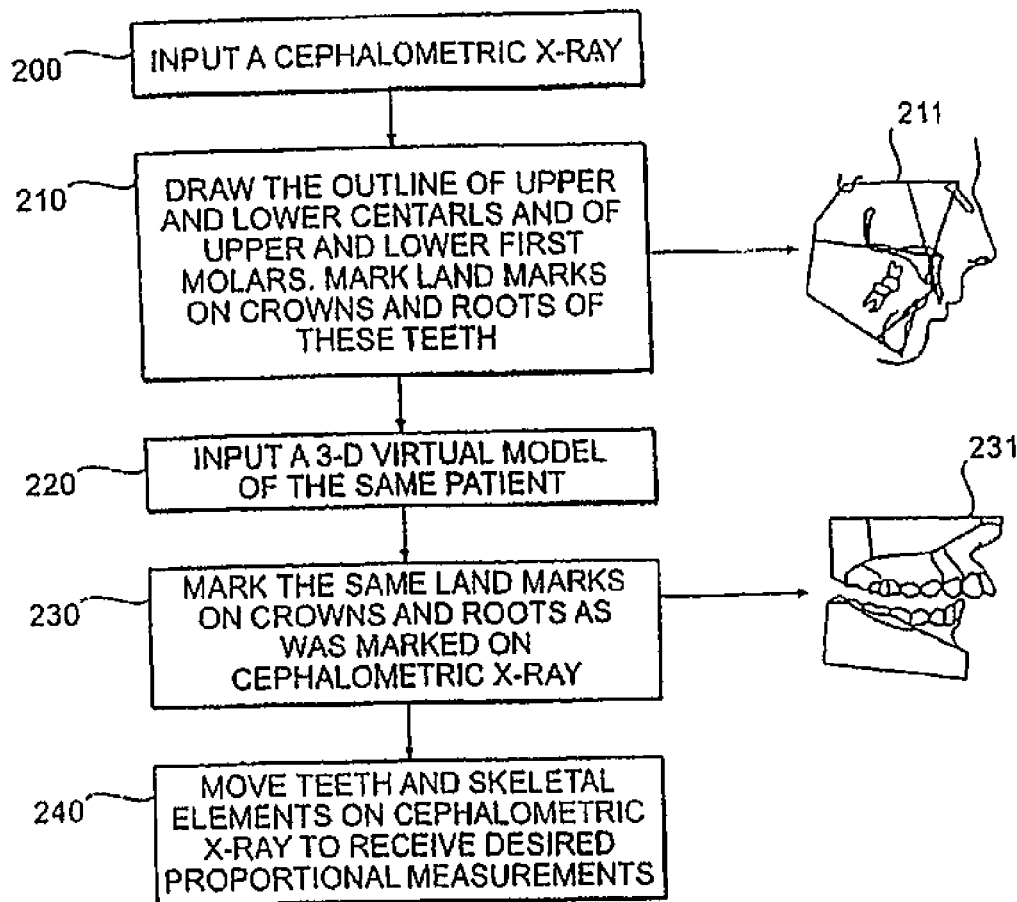
Figure 8B:
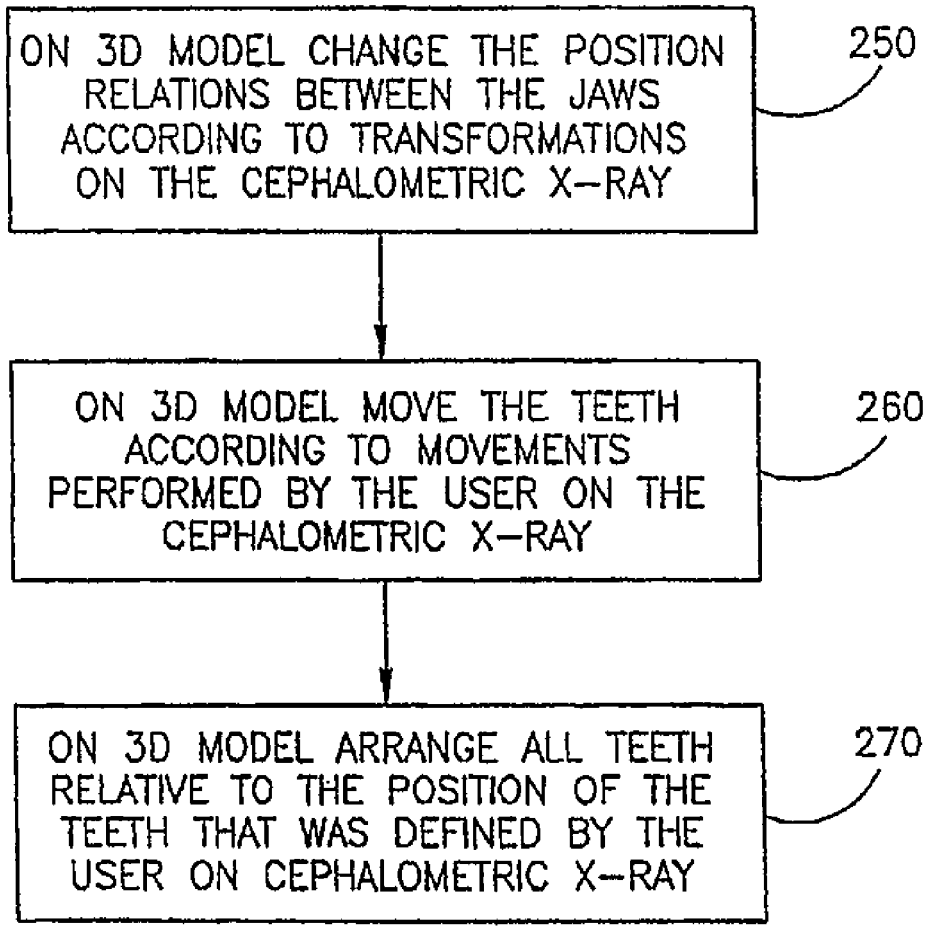

The reverse sequence of operation, namely the mapping of each point from a cephalometric image to a three-dimensional virtual teeth model is seen in FIGS. 8A and 8B. In FIG. 8A and FIG. 8B, each of steps 200–270 corresponds, mutatis mutandis to the steps 100–170 in FIGS. 7A and 7B. This eventually results in mapping of each point in a cephalometric image to the corresponding location of the tree-dimensional virtual teeth model to allow to translate any displacement performed on the former image to that in the latter.

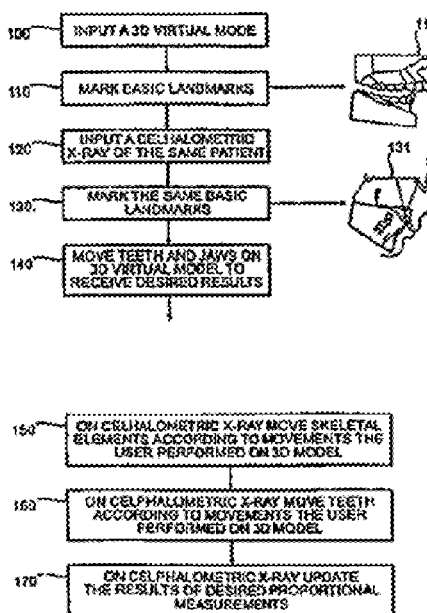

What is claimed is:

1. An image processing method comprising:
    (a) applying at least a first imaging technique and a second imaging technique to acquire a first, two-dimensional image of at least a first portion of teeth and a second three-dimensional virtual image of at least a second portion of the teeth, respectively, there being at least a partial overlap between said first and second portions; and (b) defining a set of basic anatomical landmarks in either one of the two images, locating said set in the other of the two images and registering said set in the two images.

2. A method according to claim 1, wherein said first image is a longitudinal cross-sectional image.

3. A method according to claim 2, wherein said first imaging technique is a radiographic x-ray technique.

4. A method according to claim 3, wherein said first image is cephalometric image.

5. A method according to any one of claims 1–4, wherein step (a) comprises applying a third imaging technique to acquire a third image comprising at least a profile of facial aspects.

6. A method according to any of claims 1–4, wherein said three-dimensional image comprises substantially all teeth of at least one jaw, and the two-dimensional image is positioned on the mid palatal plane of the three-dimensional image.

7. A method according to claim 1, comprising the following step: (c) displacing at least one tooth in at least one of the images in a manner resembling the manner in which said at least one tooth can be shifted in real-life orthodontic treatment; and (d) by applying a set of rules which define manner in which each element in one image maps to a corresponding element in the other image, displacing said at least one tooth in said other image.

8. A method according to claim 7, wherein said set of rules comprise defining in said one image at least one object-associated landmark of said at least one tooth, locating said object-associated landmark, and displacing said object-associated landmark in said other image, in proportion to its movement in said one image.

9. A method according to claim 8, wherein said basic landmarks are fixed, the displacement of the at least one object-associated landmark in said one image is defined according to said basic landmarks and said at least one object-associated landmark is then displaced in the same relative displacement in respect of the basic landmarks in said other image.

10. A method according to any one of claims 7–9, wherein said one image is a virtual three-dimensional image of a teeth model and said other image is a lateral image.

11. A method according to claim 10, wherein said lateral image is a cephalometric image.

12. A method according to claim 11, comprising the following step: (e) by applying a set of rules defining displacement of soft facial tissue caused by displacement of said at least one tooth, predicting effect of the displacement of said at least one tooth in said virtual three-dimensional image on soft facial tissue image in said lateral image.

13. A method according to claim 12, wherein the displacement of said soft tissue is predicted using a third image of at least a profile of facial aspects.

14. An image processing system comprising: (i) a first input utility for receipt of first data representative of a first two-dimensional cross-sectional image of at least a first teeth portion; (ii) a second input utility for receipt of second data representative of a second, tree-dimensional virtual image of teeth model of at least a second teeth portion; (iii) a module for defining basic landmarks in both images and for generating data representative thereof; and (iv) a processor associated with said first and said second input utility and with said module, for receiving said first and said second data and for mapping elements in one of the two images to the other of the two images according to the data representative of said basic landmarks.

15. A system according to claim 14, wherein said first image is a cephalometric image.

16. A system according to claim 15, comprising a third utility for receipt of third data representative of a third image comprising at least a profile of facial aspects.

17. A system according to claim 14, wherein the first, second and third utilities are integral.

18. A system according to claim 14, wherein said second utility comprises a data transferring module for transferring data representative of the second, virtual three-dimensional image to the processor.

19. A system according to claim 14, comprising a module defining a set of rules for displacing at least one virtual tooth representation in one of the images.

20. A system according to claim 19, wherein said set of rules define a displacement representing the manner of shifting of the at least one tooth in a real-life orthodontic treatment.

21. A system according to claim 19, wherein said processor translates the displacement of said at least one virtual tooth representation in one of the images to displacement of a corresponding tooth in the other image.

22. A system according to claim 21, wherein said one of the images is a virtual three-dimensional image of teeth model, and the other image is a cephalometric image.

23. A system according to claim 22, comprising a module defining a set of rules for predicting the effect of displacement of teeth in the cephalometric image of soft facial tissue.

* * * * *

UNITED STATES PATENT AND TRADEMARK OFFICE
CERTIFICATE OF CORRECTION

| | | |
|---|---|---|
| PATENT NO. | : 6,845,175 B2 | Page 1 of 11 |
| APPLICATION NO. | : 09/830264 | |
| DATED | : January 18, 2005 | |
| INVENTOR(S) | : Avi Kopeloman et al. | |

It is certified that error appears in the above-identified patent and that said Letters Patent is hereby corrected as shown below:

Delete the title page and substitute therefore the attached title page.

Delete Drawing Sheets 1-11 and substitute therefore the attached Drawing Sheets 1-9.

Signed and Sealed this

Twenty-first Day of August, 2007

JON W. DUDAS
*Director of the United States Patent and Trademark Office*

United States Patent
Kopelman et al.

(10) Patent No.: US 6,845,175 B2
(45) Date of Patent: Jan. 18, 2005

(54) DENTAL IMAGE PROCESSING METHOD AND SYSTEM

(75) Inventors: Avi Kopelman, Tel Aviv (IL); Eldad Taub, Reut (IL)

(73) Assignee: Cadent Ltd., Or Yehuda (IL)

(*) Notice: Subject to any disclaimer, the term of this patent is extended or adjusted under 35 U.S.C. 154(b) by 479 days.

(21) Appl. No.: 09/830,264

(22) Filed: Apr. 23, 2001

(65) Prior Publication Data
US 2003/0169913 A1 Sep. 11, 2003

Related U.S. Application Data

(63) Continuation of application No. PCT/IL99/00577, filed on Nov. 1, 1999.

(30) Foreign Application Priority Data

Nov. 1, 1998 (IL) .................................. 126838

(51) Int. Cl.⁷ .................................. G06K 9/00
(52) U.S. Cl. .................. 382/154; 382/294; 128/922
(58) Field of Search .................. 382/128, 131, 382/154, 285, 294; 600/587, 589, 590; 128/922; 433/24, 29, 68, 69, 215

(56) References Cited

U.S. PATENT DOCUMENTS

| | | |
|---|---|---|
| 5,151,856 A | 9/1992 | Halmann et al. |
| 5,278,756 A | 1/1994 | Lemchen et al. |
| 5,318,441 A * | 6/1994 | Keller .................. 433/68 |
| 6,068,482 A * | 5/2000 | Snow .................. 433/223 |
| 6,081,739 A * | 6/2000 | Lemchen .................. 600/407 |

FOREIGN PATENT DOCUMENTS

| | | |
|---|---|---|
| DE | 4141311 | 8/1993 |
| EP | 0488987 | 6/1992 |
| EP | 0741994 | 11/1996 |
| JP | 4-336048 | 11/1992 |
| WO | WO 97/03022 | 2/1997 |
| WO | 01/80761 A2 | 11/2001 |

OTHER PUBLICATIONS

International Search Report for International Application No. PCT/IL 99/00577, mailed on Feb. 17, 2000.

An English language title and abstract is provided for DE 4141311.

* cited by examiner

*Primary Examiner*—Todd E. Manahan
(74) *Attorney, Agent, or Firm*—Nath & Associates PLLC; Gary M. Nath; Lee C. Heiman

(57) ABSTRACT

An image processing method for use in dentistry or orthodontic is provided. Two images of teeth, one being a two-dimensional image and one a three-dimensional image are combined in a manner to allow the use of information obtained from one to the other. In order to combine the two images a set of basic landmarks is defined in one, identified in the other and then the two images are registered.

23 Claims, 9 Drawing Sheets

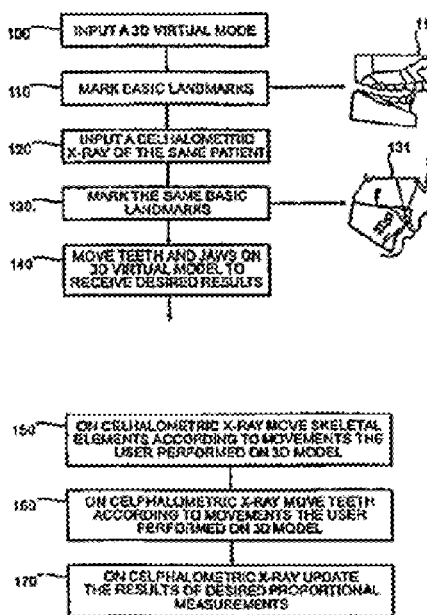

UNITED STATES PATENT AND TRADEMARK OFFICE
CERTIFICATE OF CORRECTION

PATENT NO. : 6,845,175 B2
APPLICATION NO. : 09/830264
DATED : January 18, 2005
INVENTOR(S) : Avi Kopelman et al.

It is certified that error appears in the above-identified patent and that said Letters Patent is hereby corrected as shown below:

Delete the title page and substitute therefore the attached title page.

Delete Drawing Sheets 1-11 and substitute therefore the attached Drawing Sheets 1-9.

This certificate supersedes Certificate of Correction issued August 21, 2007.

Signed and Sealed this

Eighteenth Day of September, 2007

JON W. DUDAS
*Director of the United States Patent and Trademark Office*

United States Patent
Kopelman et al.

(10) Patent No.: US 6,845,175 B2
(45) Date of Patent: Jan. 18, 2005

(54) DENTAL IMAGE PROCESSING METHOD AND SYSTEM

(75) Inventors: Avi Kopelman, Tel Aviv (IL); Eldad Taub, Reut (IL)

(73) Assignee: Cadent Ltd., Or Yehuda (IL)

(*) Notice: Subject to any disclaimer, the term of this patent is extended or adjusted under 35 U.S.C. 154(b) by 479 days.

(21) Appl. No.: 09/830,264

(22) Filed: Apr. 23, 2001

(65) Prior Publication Data
US 2003/0169913 A1 Sep. 11, 2003

Related U.S. Application Data

(63) Continuation of application No. PCT/IL99/00577, filed on Nov. 1, 1999.

(30) Foreign Application Priority Data
Nov. 1, 1998 (IL) .................................. 126838

(51) Int. Cl.⁷ .................................. G06K 9/00
(52) U.S. Cl. .................. 382/154; 382/294; 128/922
(58) Field of Search .................. 382/128, 131, 382/154, 285, 294; 600/587, 589, 590; 128/922; 433/24, 29, 68, 69, 215

(56) References Cited

U.S. PATENT DOCUMENTS

| | | |
|---|---|---|
| 5,151,856 A | 9/1992 | Haimann et al. |
| 5,278,756 A | 1/1994 | Lemchen et al. |
| 5,318,441 A * | 6/1994 | Keller .................. 433/68 |
| 6,068,482 A * | 5/2000 | Snow .................. 433/223 |
| 6,081,739 A * | 6/2000 | Lemchen .................. 600/407 |

FOREIGN PATENT DOCUMENTS

| | | |
|---|---|---|
| DE | 4141311 | 8/1993 |
| EP | 0488987 | 6/1992 |
| EP | 0741994 | 11/1996 |
| JP | 4-336048 | 11/1992 |
| WO | WO 97/03022 | 2/1997 |
| WO | 01/80761 A2 | 11/2001 |

OTHER PUBLICATIONS

International Search Report for International Application No. PCT/IL 99/00577, mailed on Feb. 17, 2003.

An English language title and abstract is provided for DE 4141311.

* cited by examiner

*Primary Examiner*—Todd E. Manahan
(74) *Attorney, Agent, or Firm*—Nath & Associates PLLC; Gary M. Nath; Lee C. Heiman

(57) ABSTRACT

An image processing method for use in dentistry or orthodontic is provided. Two images of teeth, one being a two-dimensional image and one a three-dimensional image are combined in a manner to allow the use of information obtained from one to the other. In order to combine the two images a set of basic landmarks is defined in one, identified in the other and then the two images are registered.

23 Claims, 9 Drawing Sheets